(12) United States Patent
Turner, Jr. et al.

(10) Patent No.: US 10,460,078 B2
(45) Date of Patent: Oct. 29, 2019

(54) SYSTEMS AND METHODS FOR REMOTE DEMAND BASED DATA MANAGEMENT OF CLINICAL LOCATIONS

(71) Applicant: PARALLEL 6, INC., San Diego, CA (US)

(72) Inventors: David Wayne Turner, Jr., San Diego, CA (US); Bradley Malcolm Pruitt, San Diego, CA (US)

(73) Assignee: Parallel 6, Inc., San Diego, CA (US)

( * ) Notice: Subject to any disclaimer, the term of this patent is extended or adjusted under 35 U.S.C. 154(b) by 0 days.

(21) Appl. No.: 15/475,088

(22) Filed: Mar. 30, 2017

(65) Prior Publication Data
US 2017/0228501 A1   Aug. 10, 2017

Related U.S. Application Data

(63) Continuation-in-part of application No. 14/738,766, filed on Jun. 12, 2015, which is a continuation-in-part
(Continued)

(51) Int. Cl.
*G06F 19/00* (2018.01)
*G16H 10/20* (2018.01)
(Continued)

(52) U.S. Cl.
CPC ....... *G06F 19/325* (2013.01); *G06Q 30/0205* (2013.01); *G06Q 30/0214* (2013.01);
(Continued)

(58) Field of Classification Search
USPC .............................................. 705/7.11–7.42
See application file for complete search history.

(56) References Cited

U.S. PATENT DOCUMENTS

| 7,711,580 B1 | 5/2010 | Hudson |
| 7,899,685 B2 | 3/2011 | Wallach et al. |

(Continued)

FOREIGN PATENT DOCUMENTS

| KR | 1020120020915 A | 3/2012 |
| KR | 1020120124856 A | 11/2012 |
| WO | 2006/047832 A1 | 5/2006 |

OTHER PUBLICATIONS

Cimino, et al., The patient clinical information system (PatCIS): technical solutions for and experience with giving patients access to their electronic medical records, International Journal of Medical Informatics 68 (2002) 113-127 (Year: 2002).*

(Continued)

*Primary Examiner* — Amber A Misiaszek
(74) *Attorney, Agent, or Firm* — Kilpatrick Townsend & Stockton LLP

(57) ABSTRACT

A system and a method for managing one or more clinical protocols across multiple locations, including identify a clinical research location; capture a plurality of types of content from the administrator mobile device; analyze the captured content to determine one or more associated clinical protocols for the clinical research location; automatically select a workflow algorithm for each determined clinical protocol, the workflow algorithm configured to obtain stage based information and workflow items from the data store; and enable a mobile control interface for each determined clinical protocol, wherein the mobile control interface comprises monitoring of the stage based information and management of the workflow items associated with the clinical research location.

17 Claims, 15 Drawing Sheets

Related U.S. Application Data of application No. 14/507,735, filed on Oct. 6, 2014, which is a continuation of application No. 14/092,882, filed on Nov. 27, 2013, now Pat. No. 8,856,031, application No. 15/475,088, which is a continuation of application No. 13/487,155, filed on Jun. 1, 2012, which is a continuation of application No. 14/214,653, filed on Mar. 14, 2014, which is a continuation of application No. 13/373,856, filed on Dec. 2, 2011.

(60) Provisional application No. 62/315,535, filed on Mar. 30, 2016, provisional application No. 61/798,358, filed on Mar. 15, 2013, provisional application No. 61/492,359, filed on Jun. 1, 2011, provisional application No. 61/785,803, filed on Mar. 14, 2013, provisional application No. 61/460,036, filed on Dec. 23, 2010, provisional application No. 61/458,897, filed on Dec. 3, 2010.

(51) Int. Cl.
    *H04L 29/08* (2006.01)
    *G06Q 30/02* (2012.01)
    *G06Q 50/00* (2012.01)
    *H04W 4/04* (2009.01)

(52) U.S. Cl.
    CPC ..... *G06Q 30/0226* (2013.01); *G06Q 30/0241* (2013.01); *G06Q 30/0277* (2013.01); *G16H 10/20* (2018.01); *H04L 67/025* (2013.01); *H04L 67/04* (2013.01); *H04L 67/10* (2013.01); *H04L 67/125* (2013.01); *H04L 67/18* (2013.01); *H04L 67/22* (2013.01); *H04L 67/26* (2013.01); *H04L 67/32* (2013.01); *H04W 4/04* (2013.01); *G06Q 50/01* (2013.01)

(56) References Cited

U.S. PATENT DOCUMENTS

| | | | |
|---|---|---|---|
| 7,953,654 B2 | 5/2011 | Abifaker | |
| 8,312,079 B2 | 11/2012 | Newsome et al. | |
| 8,386,322 B2 | 2/2013 | Williams et al. | |
| 8,402,387 B1 | 3/2013 | Iversen | |
| 8,548,849 B1 | 10/2013 | Porter | |
| 8,611,871 B2 | 12/2013 | Terrell, II | |
| 8,856,031 B1* | 10/2014 | Turner, Jr. | G06Q 30/0241 705/14.66 |
| 2002/0062228 A1 | 5/2002 | Portnoy et al. | |
| 2002/0069037 A1 | 6/2002 | Hendrickson et al. | |
| 2002/0069116 A1 | 6/2002 | Ohashi et al. | |
| 2003/0130871 A1 | 7/2003 | Rao et al. | |
| 2003/0139942 A1 | 7/2003 | Rakshit et al. | |
| 2003/0204418 A1 | 10/2003 | Ledley | |
| 2004/0010418 A1* | 1/2004 | Buonocore | G06F 19/325 705/2 |
| 2004/0064344 A1 | 4/2004 | Link et al. | |
| 2005/0149397 A1 | 7/2005 | Morgenstern et al. | |
| 2005/0182657 A1 | 8/2005 | Abraham-Fuchs et al. | |
| 2005/0193335 A1 | 9/2005 | Dorai et al. | |
| 2005/0234781 A1 | 10/2005 | Morgenstern et al. | |
| 2005/0243784 A1 | 11/2005 | Fitzgerald et al. | |
| 2006/0129433 A1 | 6/2006 | Koneru | |
| 2006/0161599 A1 | 7/2006 | Rosen | |
| 2006/0224421 A1 | 10/2006 | St. Ores et al. | |
| 2006/0256133 A1 | 11/2006 | Rosenberg | |
| 2006/0259360 A1 | 11/2006 | Flinn et al. | |
| 2006/0259361 A1 | 11/2006 | Barhydt et al. | |
| 2006/0282292 A1 | 12/2006 | Brink et al. | |
| 2007/0005424 A1 | 1/2007 | Arauz | |
| 2007/0258626 A1 | 11/2007 | Reiner | |
| 2007/0265917 A1 | 11/2007 | Belanger et al. | |
| 2008/0228582 A1 | 9/2008 | Fordyce et al. | |
| 2008/0300915 A1 | 12/2008 | Molmenti et al. | |
| 2009/0089098 A1 | 4/2009 | Schoenberg | |
| 2009/0093688 A1 | 4/2009 | Mathur | |
| 2009/0150215 A1 | 6/2009 | Kalb et al. | |
| 2009/0164245 A1 | 6/2009 | Toleti et al. | |
| 2009/0198579 A1 | 8/2009 | Lewis et al. | |
| 2009/0271289 A1 | 10/2009 | Klinger et al. | |
| 2009/0288012 A1 | 11/2009 | Hertel et al. | |
| 2009/0298480 A1 | 12/2009 | Khambete et al. | |
| 2009/0299856 A1 | 12/2009 | Caunter | |
| 2009/0313048 A1 | 12/2009 | Kahn et al. | |
| 2010/0015991 A1 | 1/2010 | Evans et al. | |
| 2010/0036719 A1 | 2/2010 | Eklund | |
| 2010/0042471 A1 | 2/2010 | Chang et al. | |
| 2010/0042487 A1 | 2/2010 | Barazani | |
| 2010/0062794 A1 | 3/2010 | Han | |
| 2010/0088245 A1 | 4/2010 | Harrison et al. | |
| 2010/0094650 A1 | 4/2010 | Tran et al. | |
| 2010/0106577 A1 | 4/2010 | Grimes | |
| 2010/0250285 A1 | 9/2010 | Shelton | |
| 2010/0332258 A1 | 12/2010 | Dahlke et al. | |
| 2011/0015987 A1 | 1/2011 | Chakraborty et al. | |
| 2011/0047013 A1 | 2/2011 | McKenzie, III | |
| 2011/0072107 A1 | 3/2011 | Gutta et al. | |
| 2011/0093292 A1* | 4/2011 | Hussam | G06Q 10/06 705/3 |
| 2011/0119075 A1 | 5/2011 | Dhoble | |
| 2011/0153361 A1* | 6/2011 | Hanina | G06Q 10/10 705/3 |
| 2011/0161167 A1 | 6/2011 | Jallapuram | |
| 2011/0191184 A1 | 8/2011 | Blackhurst et al. | |
| 2011/0238495 A1 | 9/2011 | Kang | |
| 2011/0246287 A1 | 10/2011 | Wright et al. | |
| 2011/0264494 A1 | 10/2011 | Lechowicz | |
| 2011/0270617 A1 | 11/2011 | Pacheco E Murta et al. | |
| 2011/0295703 A1 | 12/2011 | Flinn et al. | |
| 2011/0306846 A1 | 12/2011 | Osorio | |
| 2011/0307340 A1 | 12/2011 | Benmbarek | |
| 2011/0307917 A1 | 12/2011 | Shuster | |
| 2011/0320967 A1 | 12/2011 | Knitowski et al. | |
| 2012/0131570 A1 | 5/2012 | Kaikkonen et al. | |
| 2012/0150598 A1 | 6/2012 | Griggs | |
| 2012/0158420 A1 | 6/2012 | Lacal et al. | |
| 2012/0179480 A1 | 7/2012 | Patel et al. | |
| 2012/0215617 A1 | 8/2012 | Shah et al. | |
| 2012/0246003 A1 | 9/2012 | Hart et al. | |
| 2012/0284108 A1 | 11/2012 | Fontana et al. | |
| 2012/0310670 A1 | 12/2012 | Pruitt | |
| 2013/0006705 A1 | 1/2013 | Votaw et al. | |
| 2013/0080239 A1 | 3/2013 | Okerlund | |
| 2013/0211904 A1 | 8/2013 | Bax et al. | |
| 2013/0262494 A1 | 10/2013 | Petersen et al. | |
| 2013/0297340 A1 | 11/2013 | Van Zon et al. | |
| 2013/0332235 A1 | 12/2013 | Kuppusamy | |
| 2014/0032656 A1 | 1/2014 | Hyman et al. | |
| 2017/0228501 A1* | 8/2017 | Turner, Jr. | G06F 19/325 |

OTHER PUBLICATIONS

Non-Final Office Action for U.S. Appl. No. 13/487,155 dated, Nov. 16, 2017, 34 pages.

Non-Final Office Action for U.S. Appl. No. 14/214,653 dated, Oct. 30, 2017, 32 pages.

Janofsky et al., "The Hopkins Competency Assessment Test: A Brief Method for Evaluating Patients' Capacity to Give Informed Consent", Hospital and Community Psychiatry, vol. 43, No. 2, 1992, pp. 132-136.

International Search Report and Written Opinion for PCT/US2017/025213 dated, Jun. 30, 2017, 10 pages.

EESR dated Nov. 2, 2016 for EP Patent Application No. 14763461.2 (7 pages).

International Search Report and Written Opinion dated Aug. 6, 2014, in corresponding International Application No. PCT/US2014/030900, 11 pages.

Janofsky. "The Hopkins Competency Assessment Test: A Brief Method for Evaluating Patients' Capacity to Give Informed Consent." Hospital and Community Psychiatry. 43(2):132-136 (Feb. 1992).

(56) References Cited

OTHER PUBLICATIONS

International Search Report and Written Opinion for related PCT Application No. PCT/US2017/025213, dated Jun. 30, 2017.
Final Office Action for U.S. Appl. No. 14/214,653 dated Jul. 5, 2018, 30 pages.
Final Office Action for U.S. Appl. No. 13/487,155 dated Sep. 7, 2018, 19 pages.
International Preliminary Report on Patentability for PCT/US2017/025213 dated Oct. 11, 2018, 9 pages.
Non-Final Office Action for U.S. Appl. No. 13/373,856 dated Mar. 8, 2019, 16 pages.
Non-Final Office Action for U.S. Appl. No. 14/214,653 dated Mar. 13, 2019, 28 pages.
Non Final Office Action for U.S. Appl. No. 13/487,155 dated Jan. 9, 2019, 17 pages.
Final Office Action for U.S. Appl. No. 13/487,155 dated Jul. 5, 2019, 13 pages.
Final Office Action for U.S. Appl. No. 13/487,155 dated Aug. 12, 2019, 16 pages.

* cited by examiner

SYSTEMS AND METHODS FOR REMOTE DEMAND BASED DATA MANAGEMENT OF CLINICAL LOCATIONS

CROSS-REFERENCE TO RELATED APPLICATIONS

This application claims priority to U.S. Provisional Patent Application No. 62/315,535, filed Mar. 30, 2016. This application is also a continuation-in-part of U.S. patent application Ser. No. 14/738,766, filed on Jun. 12, 2015, which is a continuation-in-part of U.S. Pat. No. 10,147,109, issued on Dec. 4, 2018, which claims priority as a continuation of U.S. Pat. No. 8,856,031, issued on Oct. 7, 2014, which claims priority to U.S. Provisional Patent Application No. 61/798,358, filed on Mar. 15, 2013, all of which are incorporated herein by reference. This application is also a continuation-in-part of U.S. patent application Ser. No. 13/373,856, filed on Dec. 2, 2011, which claims priority to U.S. Provisional Patent Application No. 61/460,036 filed on Dec. 23, 2010 and U.S. Provisional Patent Application No. 61/458,897 filed on Dec. 3, 2010, all of which are incorporated herein by reference. This application is also a continuation-in-part of U.S. patent application Ser. No. 13/487,155, filed on Jun. 1, 2012, which claims priority to U.S. Provisional Patent Application No. 61/492,359, filed on Jun. 1, 2011, all of which are incorporated herein by reference. This application is also a continuation-in-part of U.S. patent application Ser. No. 14/214,653, filed on Mar. 14, 2014, which claims priority to U.S. Provisional Patent App. No. 61/785,803, filed on Mar. 14, 2013, all of which are incorporated herein by reference.

TECHNICAL FIELD

The embodiments described herein are related to the field of mobile technology and mobile platforms that gather and store information and more specifically to systems and methods that enable remote demand based management of research at multiple location.

BACKGROUND

A clinical research administrator, also referred to as a clinical monitor or trial monitor, is a health-care professional that performs activities related to medical research, particularly clinical trials. Clinical research administrators work in various settings, such as pharmaceutical companies, medical research institutes and government agencies.

A key responsibility of a clinical research administrator is to monitor clinical trials. In some examples, an administrator may work directly with a sponsor company of a clinical trial, as an independent freelancer or for a contract research organization. A clinical research administrator is typically responsible for a number of duties across multiple locations that involve a large amount of time and coordination.

Several clinical trials are often conducted at a clinical site (medical practice office, hospital or specialized clinic) and require periodic participation by the patients over a long period of time, from as little as a few days to many years. The patients typically come to the clinical site numerous times for periods of time to receive treatments and be tested to determine the results of the treatments.

Clinical research costs are skyrocketing due to inefficient patient recruitment, delays due to patient enrollment problems, clinical trial management and An increase in the number of trials across the industry means that more and more drug companies sponsoring clinical trials need to attract the best-performing CROs, clinical sites, and physician investigators (PIs) to increase their odds for success, which only drives prices for CRO services even higher. Likewise, the number of trials at each clinical research site is increasing while the number of clinical research sites is also growing. With more research sites being used for a particular research trial, as well as, more research trials at a particular research site, the costs and complexity associated with recruitment, monitoring, management, and reporting are growing. Accordingly, clinical trial sponsors and clinical (or contract) research organizations (CROs) are desperate for solutions to improve and streamline the clinical trial process.

Conventional tools available for managing clinical trials employ legacy technology and are insufficient to scale with the growth and complexity of the clinical research industry.

Many such conventional systems fail to harness the full capabilities of technology such as mobile devices, location based information, and the ability to track location through and push messages to mobile devices to effectively manage onsite activities and gain insights about participants.

For instance, modern personal mobile devices and wearable technology (e.g., smartphone, tablet personal computer (PC), smartwatch) afford users an unprecedented level of connectivity. Users are able to upload and download data at virtually any location. However, conventional means of conducting research (e.g., clinical studies or trials) still confine the process both geographically and temporally. A study participant (e.g., patient) rarely interacts with study organizers (e.g., medical researchers) outside of designated facilities (e.g., laboratory, hospital) and scheduled appointments. Consequently, both participants and organizers may fail to capture and exchange valuable data throughout the duration of the research.

Clinical research administrators need modern tool to effectively monitor and manage compliance with clinical trial protocols, checks clinical site activities, site inspections, reviews case report forms, as well as communicate with clinical research coordinators. Clinical research administrators play an important role in assuring the protection of the rights, safety and wellbeing of human study subjects. Clinical research tools need to protect the scientific integrity of collected data collected and assure that adverse events are correctly documented and reported.

SUMMARY

An example implementation of the present disclosure include a mobile administrator platform to gather and store content and associates that content with workflow steps associated with a clinical protocol. The clinical protocol can include workflow algorithms for specific purpose, such as, starting up a clinical research site, ongoing monitoring of a clinical research site, conducting a clinical research trial, closing down a clinical research site, closing down a clinical research trial, etc.

The mobile administrator platform can include content from mobile devices to gather information from client applications, websites, location date, bio-sensor, etc., Content can include documents, certificates, videos, training materials, protocol material, licenses, sharing components, time cards, expense forms, trip reports, maps and locations, contact information, to do lists, calendar information, alerts and notifications, and other general based content.

An example aspect of the present disclosure includes a mobile administrator for interaction with mobile devices associated with a research trial to track, manage, and communicate with practitioners conducting the research trial and participants of the research trial. Accordingly to an example implementation, the mobile administrator can be used for contextual communication with mobile devices to gather and share documents, videos, and other content based on the location of the mobile device and status of the clinical research trial.

An example aspect of the present disclosure includes a mobile control interface to allow an administrator to upload documents and other content either in singular form, bulk form or input through another system via an API, and associates those documents with specific workflow steps for the purpose of starting up a clinical research site or the ongoing monitoring of a clinical or research site including but not limited to documents, certificates, videos, training materials, protocol material, licenses, sharing components, time cards, expense forms, trip reports, maps and locations, contact information, to do lists, calendar information, alerts and notifications, and other general based content. Based on the stage of clinical or research site setup, the content will then be assigned a predetermined or dynamic rules based algorithm that will associate that content with a single mobile application or group of mobile applications of users who are specifically associated with that clinical or research site for the purposes of starting up the clinical or research site, monitoring the clinical or research site, managing the clinical or research site and reporting on the clinical or research site either in general or specific operational form. The result will be to streamline the clinical or research site startup (to conduct clinical research), the monitoring of the clinical or research site conducting the clinical research, and the management of the clinical or research site conducting the clinical research as well as other general clinical or research site tasks through a mobile device.

An administrator, after associating clinical or research sites (startup, monitoring, closeout, and other) anywhere in the world, can identify when a device associated with a participant of a particular research trial is geographically onsite at a location of the particular research trial, inspect the participants progress in the research trial. For example, an administrator can inspect the participants progress by reviewing workflow items such as, document usage, time card input, general usage, compliance to the protocol, and other general tasks.

According to one aspect, a system for managing research including a plurality of clinical research trials with multiple locations via a mobile devices, including: at least one hardware processor; and one or more software modules that are configured to, when executed by the at least one hardware processor: identify a clinical research location; capture a plurality of types of content from the administrator mobile device; analyze the captured content to determine one or more associated clinical protocols for the clinical research location; automatically select a workflow algorithm for each determined clinical protocol, the workflow algorithm configured to obtain stage based information and workflow items from the data store; and enable a mobile control interface for each determined clinical protocol, wherein the mobile control interface comprises monitoring of the stage based information and management of the workflow items associated with the clinical research location.

DETAILED DESCRIPTION

Figure 1:
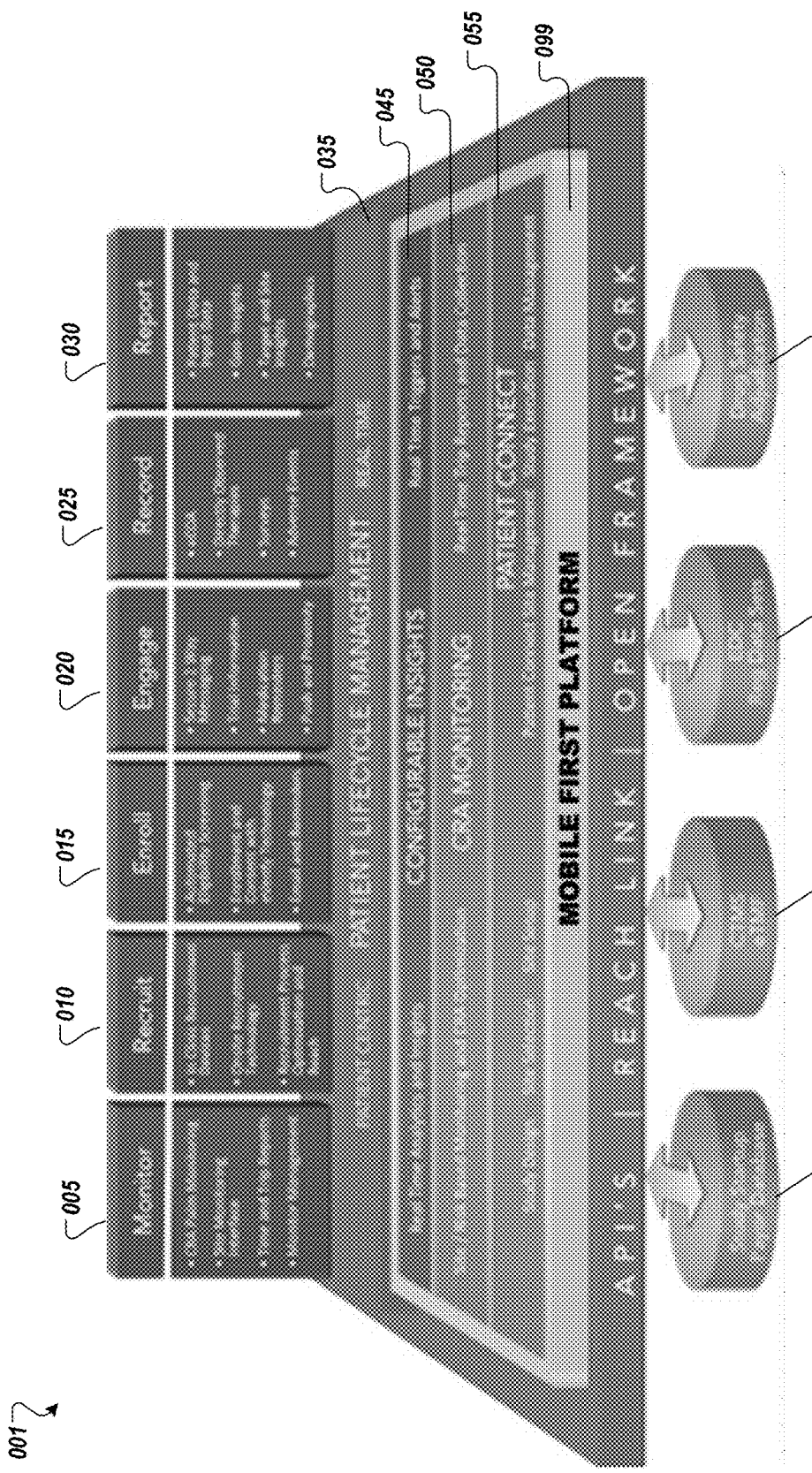
FIG. 1 is a block diagram illustrating a system for digital content and information sharing according to various embodiments.

FIG. 1 is a diagram illustrating a system 001 for digital content and information management administrator platform in accordance with one embodiment. At the core of system 011 is, for example, a distributed cloud-based mobile first administrator platform 099 configured to provide services such as insights and reporting 045, tracking and monitoring 050, and patient connection 055.

Remote services and resources can be integrated, via an open framework integration service, with resources such as data warehouses 060-076, such as, a study start-up payor database 060, a clinical trial management system for electronic trial master files 065, enterprise data centers 070, and safety and compliance information 075. Each of the data sources, databases or connected devices may be a source of personal health information such as would be found in a clinic, hospital, etc. which has a plurality of patient information stored therein in the form of electronic medical records (EMRs) and Personal Health Records (PHR). Examples of the health information database include a physician investigator (PI) database, a protocol database or Electronic Health Record (EHR) database.

The open framework integration service can also interact with other platforms, such as legacy based platforms, patient centric platforms, etc. According to one embodiment, open framework integration service can connect to a Captive Reach platform as described in reference to FIG. 10.

The services and resources are used to provide various tools to a clinical trial administrator or user of system 001. A tool suite for performing workflow functions are provided to administrators via a control interface. The tool suite can include monitoring tools 005, administrator recruitment tools 010, enrollment tools 015, engagement tools 020, recording and feedback tools 025, reporting tools 030, etc. For example, the monitoring tools 005 can gather content from various sources to monitor workflow items via the administrator platform 099, such as site based monitoring, trial performance monitoring, time and trip reports, monitor management, etc.

The administrator platform 099 can be used to build and manage enterprise strength applications that allow a clinical research location to scale up the size and/or number of hosted research trials based on insights gleaned from the patient's activity and feedback. According to another embodiment, the administrator platform 099 can be used to build and manage enterprise strength applications that allow a clinical research trial to selectively spread to other clinical research locations based on insights gleaned from the patient's activity and feedback at the other clinical research locations. The administrator platform 099 provides the ability to glean certain target insights whereby the mobile platform tracks and monitors content from patients at locations. The administrator platform 099 can gather content via tools, via upload portals (e.g., singular form, bulk form or input through another system via an API, etc.) and analyze the content to determine a target vertical.

The mobile administrator platform 099 provides administrators the ability to speed up the processes of starting up a clinical or research site, monitoring the clinical research, and closing out a clinical research trial at each of the clinical locations or research sites as it relates to a clinical protocol in a clinical trial or research study. Through the mobile administrator platform 099 the administrators can deliver contextual messaging, run reports and analytics, and view results of progress through the overall clinical or research site process.

The administrator recruitment tool 010 can be set up for any type of clinical trial from any company to help administrators identify and enroll the best qualified participants. In one embodiment, the administrator recruitment tool 010 includes a matching service that can glean target insights using patient attributes, trends, and engagement patterns to match patients with clinical research trials. Patient activity can be gathered through patient devices which are used by patients at clinical research locations, to access clinical trial information websites, or other medical systems. The administrator recruitment tool 010 allows trial administrators to directly connect with potential patients via the administrator platform 099 to help patients find clinical trials that match based on the insights.

The mobile administrator platform enables an efficient mobile first solution for doctors and other research personnel associated with a clinical trial to consume content, leverage technology and tools, and interact with content to start-up, monitor, and manage a clinical or research site, as well as other activities surrounding multi-location clinical or research site management.

Through contextual messaging, reporting, insights etc. in near real time, administrators are empowered to make valuable decisions regarding how to manage, and operationalizing clinical research protocols while improving communication among practitioners and participants. The mobile administrator platform 099 reduces the overall time to startup, monitor, manage or close out a clinical research site thereby creating overall efficiencies in the conduct of clinical research. The mobile administrator platform 099 includes modules and other software structures that allow for the complex operation of the workflow of the content.

The monitoring tool 005 and reporting tool 030 can monitor and distribute various types of content and provide access to via a front-end mobile application to provide administrators complete control and access to the content. Types of content can include any content accessible through the open framework integration service, insights and reporting 045, tracking and monitoring 050, and patient connection 055, etc. Content that is monitored by administrator platform 099 can be managed and processed so that the content is delivered (e.g., push download, notifications, alert setting, etc.) according to a delivery parameters (e.g., a schedule, threshold, location detection, etc.).

In an example, an administrator can monitor when a mobile device of a person (e.g., clinical research colleagues, patients, clinical organization, compliance workers, etc.) is interfacing with monitored content, determine a device location and clinical location history, identify a target associated with the device, determine the target's association with one or more clinical workflow algorithms, retrieve status and progress information for the workflow and/or target.

The reporting tool 030 can deliver the content to the administrator via a mobile administrator interface based on a delivery parameter. For example, the monitoring tool 005 can monitor time card entries, track a when a threshold number of time-cards are out-of-date, detect a time reporter's arrival at a clinical research location, determine one or more clinical workflow's for the time reporter, retrieve status and progress information for the workflow and/or time card. Then, the reporting tool 030 can push an alert to the time reporter that includes access to the out-of-date time cards for the workflow.

Thus, an administrator can configure priority settings and a list of clinical locations to monitor using rules-based algorithms that associate content with location-aware devices to send event-based updates to the mobile administrator platform 099. Further, the administrator can configure the mobile administrator platform 099 to deliver reports for multiple clinical trials and clinical locations as well as send update alerts with direct access to content based on status information. For example, content on the administrator platform 099 is managed through a rules based software algorithm that outlines the content as follows: content that needs to be read, content that needs to be acknowledged, content that needs to be changed in some way either through user input or other means, content that needs to be signed with a real signature, any combination of the above etc.

In the rules based algorithm of the administrator platform 099, delivery algorithms may be applied to the rules that identify rule structures and govern the content and workflow. Sample delivery algorithms may include:

i. IF content=read+ack THEN flag and promote ELSE some action ii. IF content=read+mod THEN flag AND time OR promote ELSE lock content iii. IF content=read+mod+sign THEN ((flag AND time OR promote) AND alert) AND connect sign+lock content The mobile administrator platform 099 governs all content in real time or near real time, as well as, provides offline access to content via a mobile administrator application on a device. The application can promote that content through alerting, notifications, and other mechanisms to efficiently highlight or bring attention to the content using other means for the sake of efficiency and time savings.

The mobile administrator platform 099 promotes work flow items via the mobile application and can receive additional content from the mobile application. The monitoring tool 005 and reporting tool 030 include secure communications and encryption software with audit trails and data governance recording for import, validation, and approval processes of all data inbound to the mobile administrator platform 099. Content loaded into the mobile administrator platform 099 also has the ability to be targeted based on the position location of a user's mobile device.

The mobile administrator platform 099 can utilizes location-based services to send and receive a latitude-longitude location of each user on the platform 099 for geographic segmentation. Geographic segmentation works by setting up what is called a geofence. A geofence is a pre-defined radius around a specific position-location that triggers the distribution of content to a front-end mobile application once the device's position location registers as being within the radius of the fence.

A locations database, e.g., which can be part of the data warehouse can be used for setting up a single or multiple geo-fences for a piece of content. The platform 099 can be configured to log a user's position location every time a major location change is registered by the backend platform. If the user's location is within a predefined geofence that relates to an active piece of content, the user will then receive the content on their device. Otherwise, they will not. Geofencing ensures that location specific content is only delivered to users who are in a particular geographic region for which that content is relevant, and users who are outside of that area do not receive that particular piece of content.

Information content can be general informative, clinical trial based, or educational content that the administrator would like to push to a user, users at a location, users of a clinical trial, administrators of a clinical trial, etc. Information content can include a title, image(s), and a general description for the piece of content. This type of content can also be scheduled, segmented, and geofenced based on a predefined set of parameters.

The insights service 045 of the mobile administrator platform 099 allows administrators to see reports on application usage across the entire user universe. Insights come in several forms and focus on reports detailing, for example: how users are engaging with content, where users are when they are viewing content, and other custom defined reports based on the features and functionality of the front-end application(s). Insights can be powered by an "events" architecture that is built into every connected device. The events architecture works by sending an API call to the Mobile administrator platform 099 each time a pre-defined event or action occurs on the mobile device. Using this architecture, a front-end mobile application can be setup to send an event every time a specific content is viewed, button is clicked, etc. When going through the mobile integration process, events can be defined during the requirements phase of the project cycle. These specific events are then integrated into the mobile application code for each application developed, and reports on the backend are built off of all events that are tracked and logged.

Content Insights are reports based on the events architecture that track a particular event on the mobile application related to content views. Reports can be sorted and filtered based on the type of event being tracked, and can also be broken down by date range. The Target Insights are a set of algorithms, e.g. based on verticals for particular protocols or trials. The algorithms developed are intended to locate a device, identify when that device is at or near a research location, associate that device with a clinical trial, and provide tools to manage the user of the device based on the target location, target vertical, or classification and the associated algorithm.

For example, the mobile administrator platform 099 can be set up to determine when a research patient or researcher is at or near a clinical locations as well as when the research patient or researcher is at or near their home or other location of interest loaded into the platform 099. Other information such as how long was the research patient or researcher at or near the clinical locations, how long the research patient or researcher is at or near a home location or other location of interest, etc. Further information such as how long. Thus, for example, if the system 001 determines that a research patient or researcher is nearing the clinical location, then the clinical research application built on platform 099 can be configured to message the research patient or researcher with actionable content. Moreover, in one exemplary embodiment, when it is determined that research patient or researcher is near a target location, the same type of message, for example, be pushed to the research patient or researcher device.

This type of information can also be used to allow the administrator to determine how much time the research patient or researcher are spending at or near their locations as well as how long they are spending at or near another target location, and to compare the two or run other analytics on this information.

Figure 2:
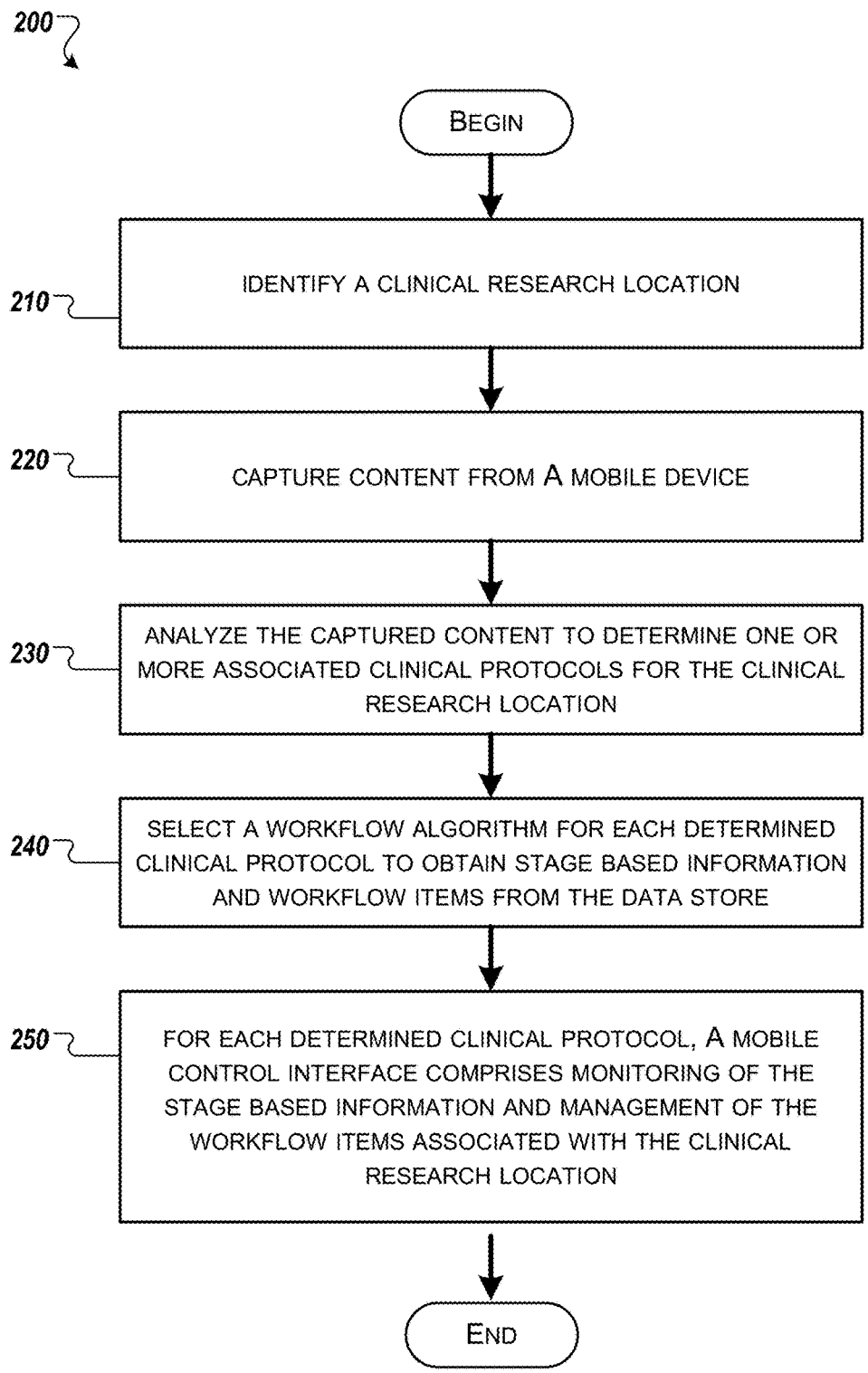
FIG. 2 is a flowchart illustrating a process for conducting research according to various embodiments.

FIG. 2 is a flow diagram illustrating an example implantation for a method 200. The method 200 is performed by processing logic that may comprise hardware (circuitry, dedicated logic, etc.), software (such as is run on a general purpose computer system or a dedicated machine), or a combination of both. Method 200 may be performed by a mobile device connected to the administrator platform 099 of FIG. 1. Though method 200 is described below as being performed by a processing device, method 200 may also be performed by other processing logic.

At block 210, the processing device identifies a clinical research location. At block 220, the processing device captures content from the mobile device. At block 230, the processing device analyzes the captured content to determine one or more associated clinical protocols for the clinical research location.

At block 240, the processing device automatically selects a workflow algorithm for each determined clinical protocol. A workflow algorithm is configured to obtain stage based information and workflow items from a data store associated with the platform.

At block 250, the processing device enables a mobile control interface for each determined clinical protocol. The mobile control interface can include monitoring of the stage based information and management of workflow items associated with the clinical research location.

Workflow items can include documents, certificates, videos, training materials, protocol material, licenses, sharing components, time cards, expense forms, trip reports, locations, contact information, to do lists, calendar information, alerts, and notifications.

The mobile control interface can include tracking of protocol activities for participants associated with the clinical research location for each clinical protocol and analytics for each clinical protocol across the multiple locations.

According to an embodiment, the processing device can present workflow items to the user via mobile control interface based on the stage based information. For example, the presented workflow item can be associated with a workflow task that requests the user to update the status of the work flow item via acknowledgement, modification, signature, or assignment. The presented workflow items can be sent via a contextual message, using the mobile control interface, to one or more devices associated with the clinical protocols The mobile control interface can include contextual messaging of devices associated with each of the clinical protocols. For example, devices associated with each clinical protocol can include participant devices, practitioner devices, facility based systems, etc. The contextual messaging can include workflow items or information assembled by the processing device. For example, the processing device can identify a recipient, alert the user based on a delivery algorithm, use information to generate a message with instructions based on the sender's or recipient's status, and prompt the user to send the message to the recipient with one or more work flow items.

The contextual messaging can be based on the participant devices or the practitioner devices detected within a radius of the clinical research location. According to an example embodiment, the contextual messaging is in view of the stage based information of the clinical protocol. This contextual messaging, produce reports, insights, etc., can be delivered or obtained in near real time allowing the administrator to make valuable decisions regarding how they are monitoring, communicating, and managing clinical research trials. Thus, key insights as to when users are interfacing with their clinical research trial, present at the clinical research site, participating in other clinical trials, or associated workflow progress and targets can be gathered with depth and insight.

Figure 3:
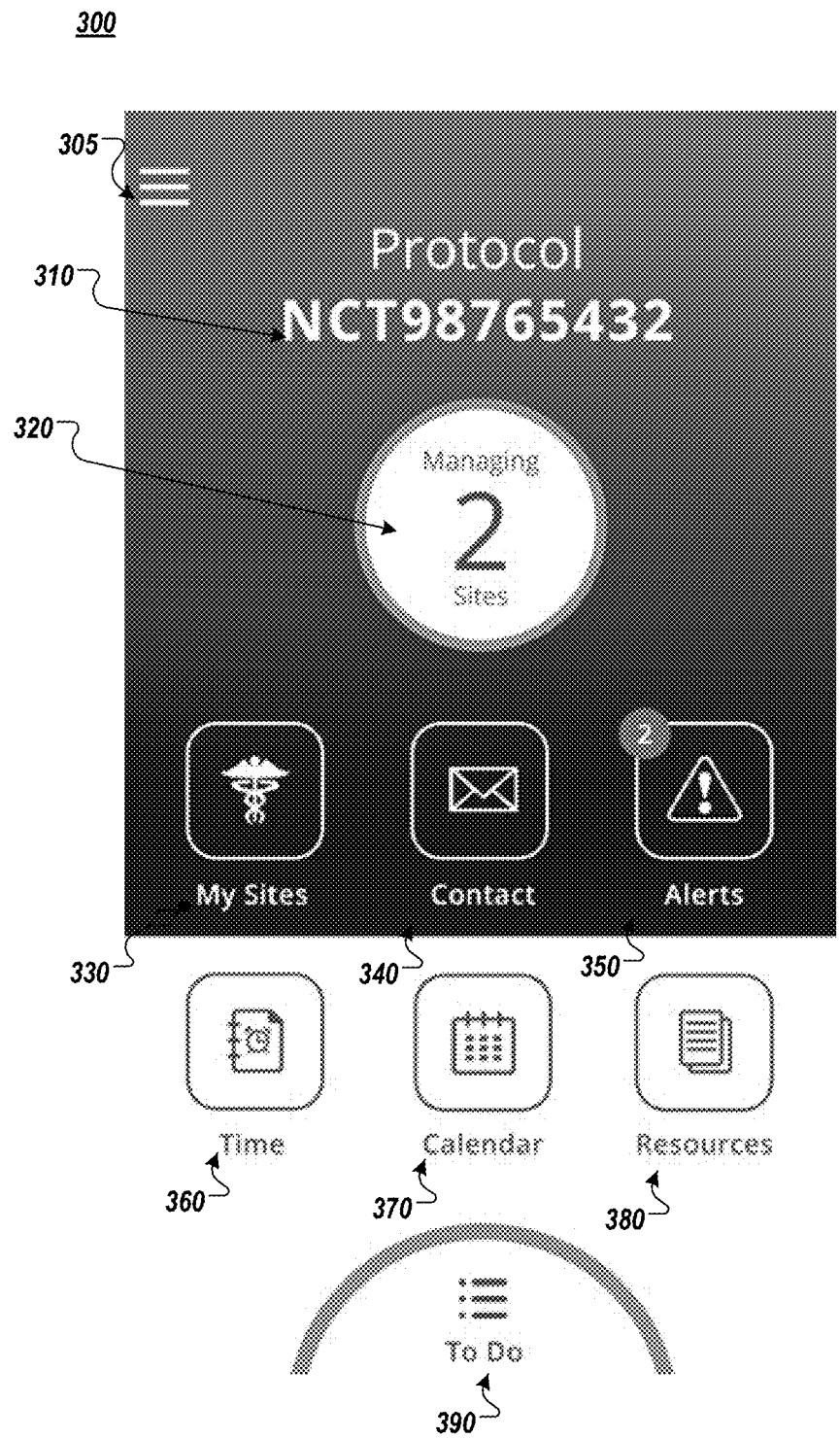
FIG. 3 is an example protocol control interface according to various embodiments.

FIG. 3 illustrates an example mobile administrator control interface 300 that allows a user to monitor and manage a clinical research trial conducted at multiple clinical research sites.

The mobile administrator control interface 300 allows the user to create lists of the clinical or research sites associated with a particular clinical research trial so that the user can see the necessary workflow and tasks for a given clinical or research site and to communicate with contextual based messaging in regard to the clinical or research site startup, monitoring, management or close out for the clinical trial.

The mobile administrator control interface 300 includes a clinical trial protocol based home screen for each trial so that the user can see the clinical or research sites, contacts and alerts associated with that protocol as well as user specific time tracking, calendaring, resources and a to do list.

In an example embodiment, the mobile administrator control interface 300 includes a global menu 305, protocol identifier 310, clinical location sites 320 for the protocol, a listing of My Sites tool 330 for clinical location sites selected by the user, a contacts tool 340 for messaging (e.g., contextual messaging), an alerts tool 350 with notification indicator for delivered items, a time card tool 360, a calendar tool 370, a resources tool 380 and a to do list tool 390.

Figure 4:
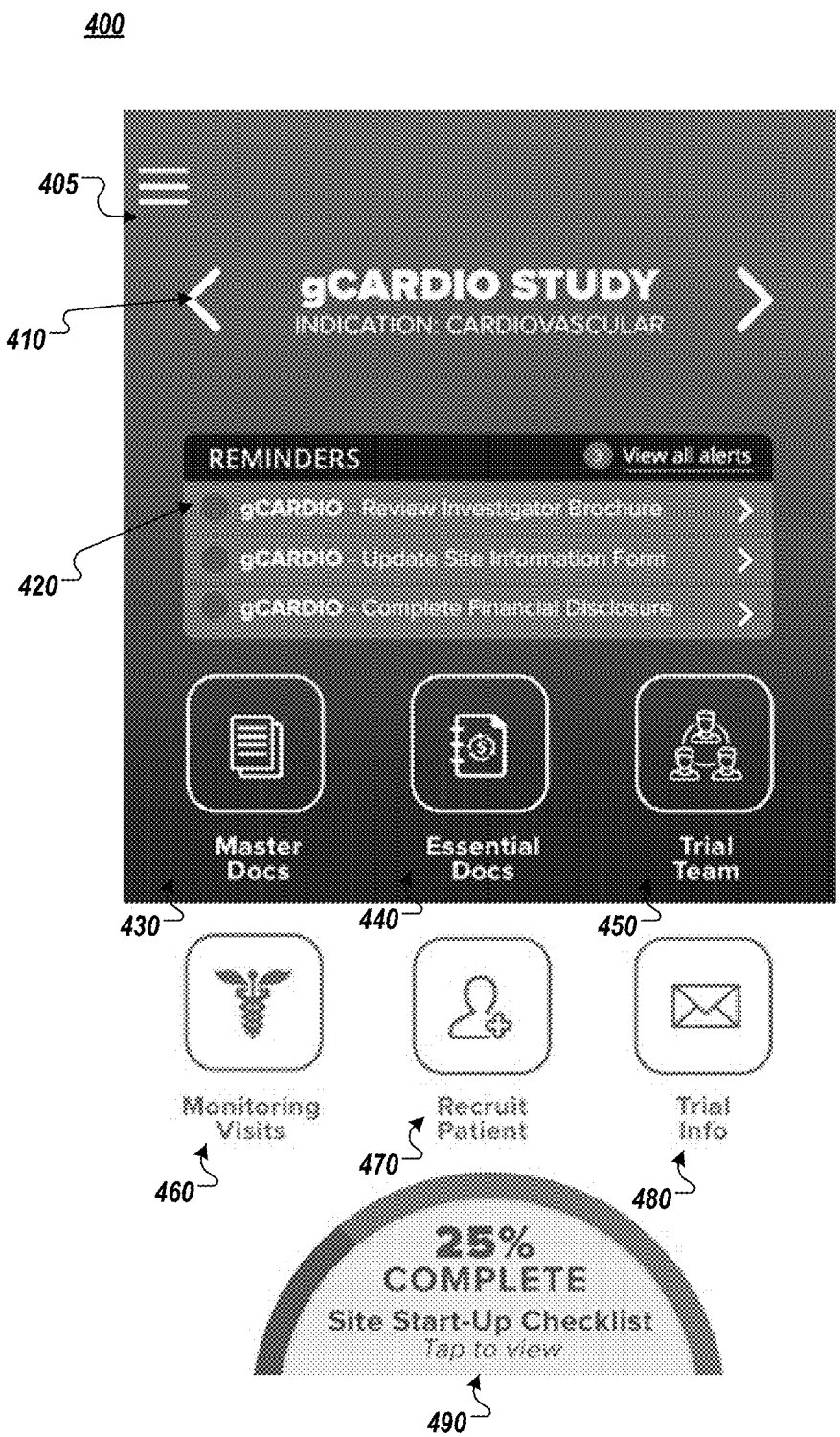
FIG. 4 is an example clinical trial control interface according to various embodiments.

FIG. 4 illustrates another example mobile administrator control interface 400 that allows a user to conduct a clinical research trial conducted at a clinical research site. The mobile administrator control interface 400 allows the user to be guided through a clinical or research site startup workflow process to collect the necessary information about the clinical research site for conducting clinical research as well as for the monitoring, management, communication and close out of that clinical or research site.

The mobile administrator control interface 400 includes a clinical trial protocol based home screen for each trial so that the user can is guided through the clinical or research site startup process so as to see the essential documents, trial team contacts, upcoming monitoring visits, trial reference information and alerts associated with that protocol as well as to recruit or invite patients to the clinical trial.

The mobile administrator control interfaces 300 and 400 provide the ability for a user controls to execute clinical or research site startup, monitoring, management, and close out for a clinical trial in an efficient manner.

The mobile administrator control interface 400 uses specific workflows algorithms and rules based structures to determine with precision, when one or more mobile application user is geographically onsite at a research location, identify the one or more users' progress on content workflow, document usage, time card input, general usage, compliance to the protocol, and other tasks via mobile devices, such as a tablet computer, mobile application, mobile enabled website, etc.

In an example embodiment, the mobile administrator control interface 400 includes a global menu 405, clinical trial navigation tool 410, a clinical trial based dashboard 420 that can update based on the clinical trial navigation tool 410, a master documents tool 430, an essential documents tool 440, a trial team tool 450, a monitoring visits tool 460, a recruit patient tool 470, a trial information tool 480, and a site based checklist 490.

FIGS. 5-10 and the corresponding description of co-pending U.S. patent application Ser. No. 14/738,766, entitled "System and methods for managing and conducting clinical or other research using a digital content and information sharing system" filed on Jun. 12, 2015, and co-pending U.S. patent application Ser. No. 13/373,856, entitled "System of Incentive Based Digital Content and Information Sharing Platform Through Mobile Technology," filed on Dec. 2, 2011, which is incorporated herein by reference as if set forth in full, provides a detailed description of example systems and methods for providing incentives to users to share offers and other special promotions provided through an application.

Figure 5:
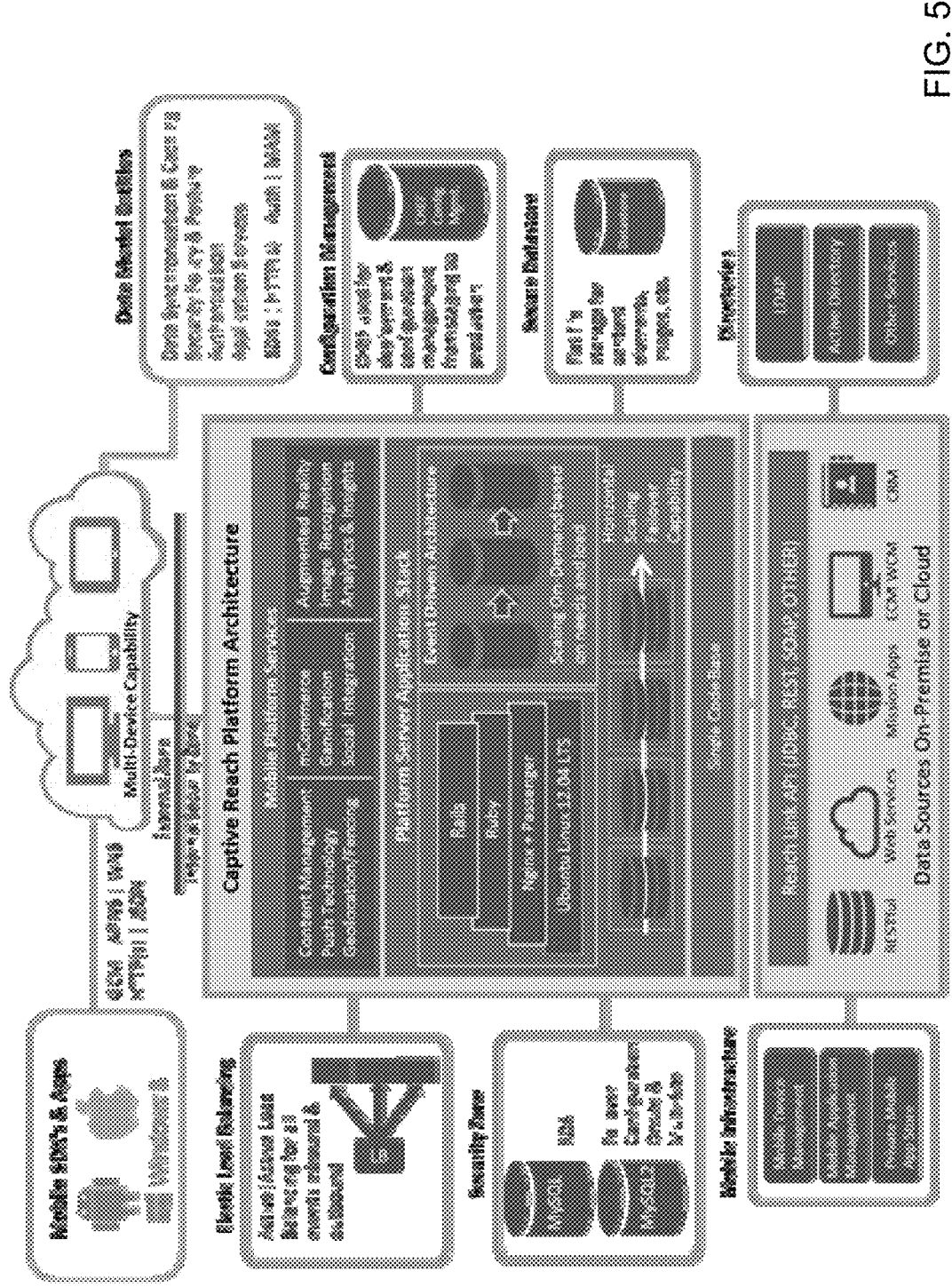
FIG. 5 is a block diagram illustrating a system for digital content and information sharing according to some alternative embodiments.

FIG. 5 is a block diagram illustrating a system 500 for digital content and information sharing according to some alternative embodiments. Referring to FIG. 5, in various embodiments, the system 500 may include a platform 510. According to one exemplary embodiment, the platform 510 may provide mobile platform services including, for example, but not limited to, content management push technology geolocation and/or fencing, mCommerce gamification social integration, and augmented reality image recognition analytics and insights. In various embodiments, the captive reach platform 510 may include a platform server application stack 512 and a single code base 514.

In various embodiments, the platform 510 may be capable of communicating with variety of devices including, for example, but not limited to, smartphones, tablet PCs, laptops, desktop PCs, and kiosks. According to one exemplary embodiment, users may interact with the platform 510 via application (e.g., Android®, iOS, and Windows®) or web portals (e.g., Safari®, FireFox®, Internet Explorer®) installed on various devices. In various embodiments, the platform 510 may access data sources 510, which may be on premise or in one or more cloud platforms, via various reach link APIs (e.g., JDBC, REST, SOAP, etc.).

Figure 6:
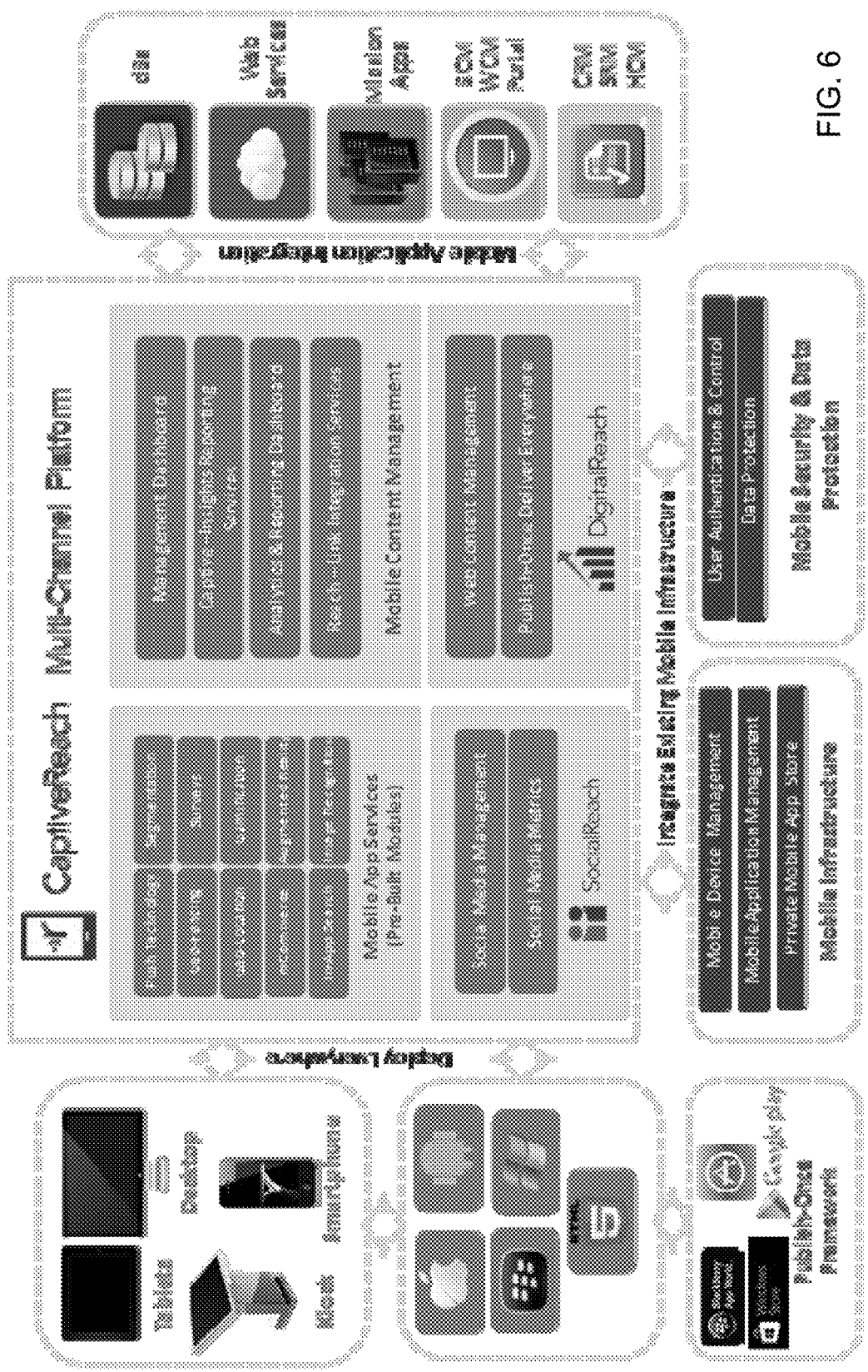
FIG. 6 is a block diagram illustrating a platform according to some alternative embodiments.

FIG. 6 is a block diagram illustrating a platform 600 according to some alternative embodiments. Referring to FIGS. 5 and 6, the platform 600 may implement the captive reach platform 510. In various embodiment, the platform 600 may be a multi-channel platform that may be deployed across different devices (e.g., smartphones, tablet PCs, laptops, desktop PCs, and kiosks) and platforms (Android®, iOS, Windows®, etc.). In various embodiments, the platform 600 may be integrated with an existing mobile infrastructure and mobile applications.

According to one exemplary embodiment, the platform 600 may provide mobile application services. The mobile application services may include pre-build modules for features including, for example, but not limited to, push technology, geo-fencing, geo-location, mCommerce, in-app search, segmentation, surveys, gamification, augmented reality, and image recognition. The platform 600 may also provide mobile content management, social media management (e.g., SocialReach), and web content management (e.g., DigitialReach).

Figure 7:
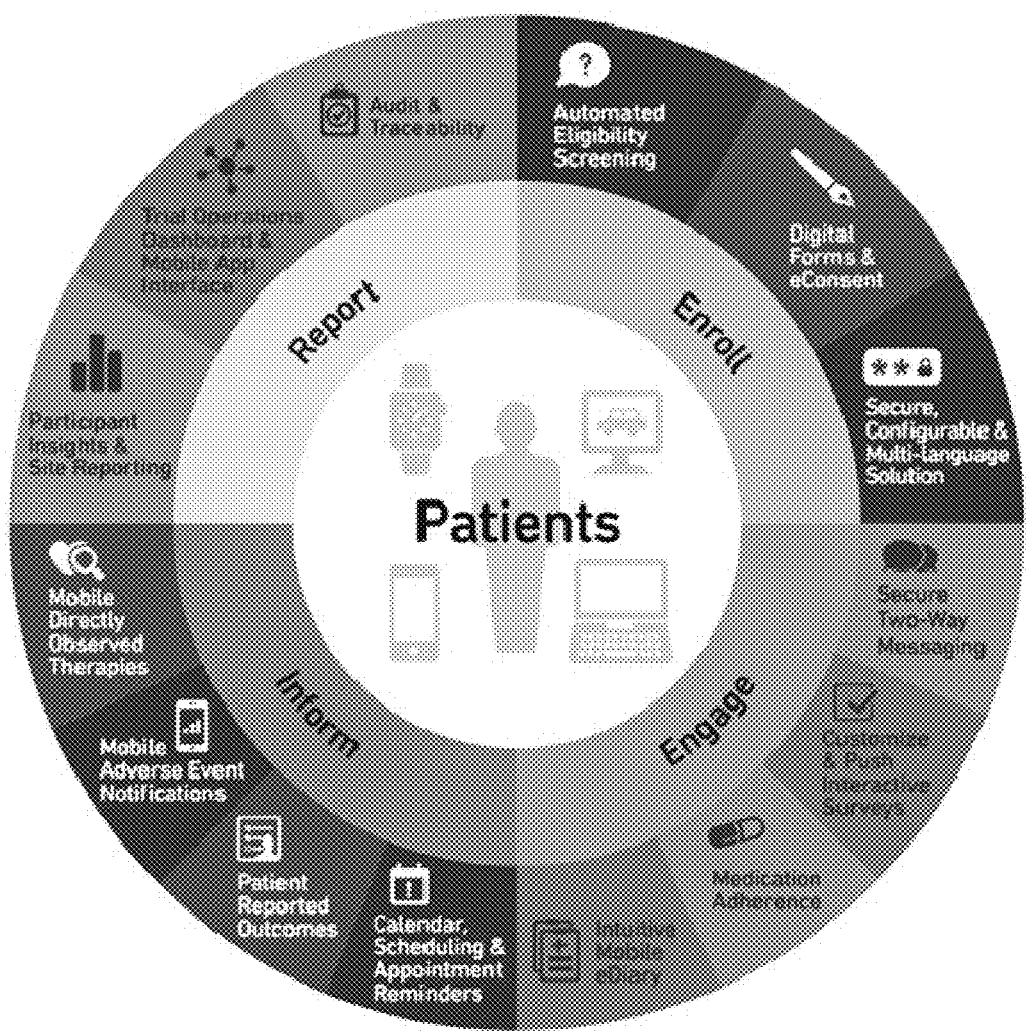
FIG. 7 is a product chart illustrating various platform modules according to various embodiments.

FIG. 7 is a product chart 700 illustrating various platform modules according to various embodiments. Referring to FIG. 7, in various embodiments, the platform modules may be categorized based on primary functionalities including, for example, but not limited to, enrollment, reporting, information, and engagement.

Figure 9:
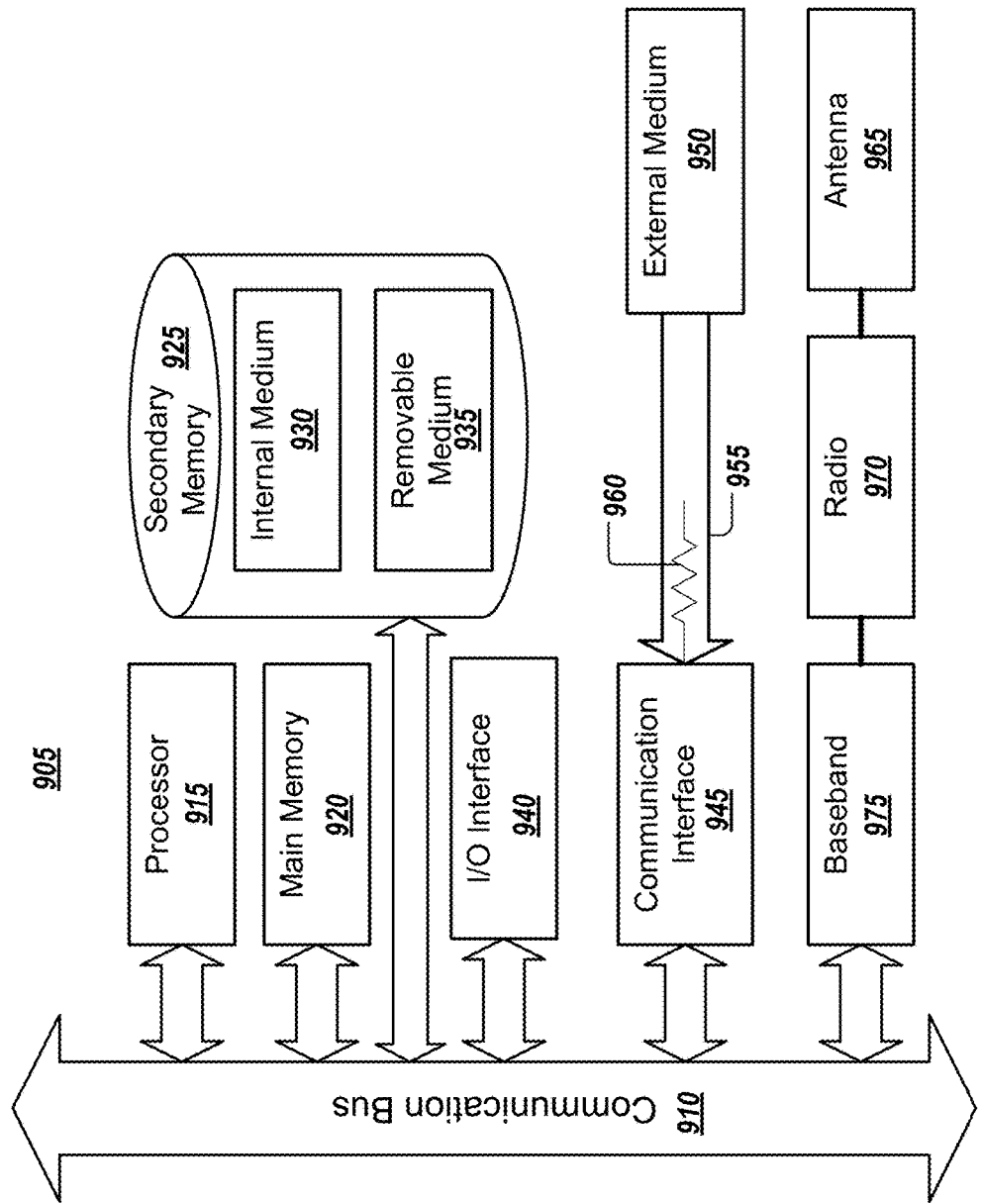
FIG. 9 is a block diagram illustrating a processing system according to various embodiments.

FIG. 9 is a block diagram illustrating an example wired or wireless system 905 that can be used in connection with various embodiments described herein. For example the system 905 can be used as or in conjunction with one or more of the mechanisms or processes described above, and may represent components of device, the corresponding backend server(s), and/or other devices described herein. The system 905 can be a server or any conventional personal computer, or any other processor-enabled device that is capable of wired or wireless data communication. Other computer systems and/or architectures may be also used, as will be clear to those skilled in the art.

The system 905 preferably includes one or more processors, such as processor 915. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 915. Examples of processors which may be used with system 905 include, without limitation, the Pentium® processor, Core i7® processor, and Xeon® processor, all of which are available from Intel Corporation of Santa Clara, Calif.

The processor 915 is preferably connected to a communication bus 910. The communication bus 910 may include a data channel for facilitating information transfer between storage and other peripheral components of the system 905. The communication bus 910 further may provide a set of signals used for communication with the processor 915, including a data bus, address bus, and control bus (not shown). The communication bus 910 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 905 preferably includes a main memory 920 and may also include a secondary memory 925. The main memory 920 provides storage of instructions and data for programs executing on the processor 915, such as one or more of the functions and/or modules discussed above. It should be understood that programs stored in the memory and executed by processor 915 may be written and/or compiled according to any suitable language, including without limitation C/C++, Java, JavaScript, Pearl, Visual Basic, .NET, and the like. The main memory 920 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 925 may optionally include an internal memory 930 and/or a removable medium 935, for example a floppy disk drive, a magnetic tape drive, a compact disc (CD) drive, a digital versatile disc (DVD) drive, other optical drive, a flash memory drive, etc. The removable medium 935 is read from and/or written to in a well-known manner. Removable storage medium 935 may be, for example, a floppy disk, magnetic tape, CD, DVD, SD card, etc.

The removable storage medium 935 is a non-transitory computer-readable medium having stored thereon computer executable code (i.e., software) and/or data. The computer software or data stored on the removable storage medium 935 is read into the system 905 for execution by the processor 915.

In alternative embodiments, secondary memory 925 may include other similar means for allowing computer programs or other data or instructions to be loaded into the system 905. Such means may include, for example, an external storage medium 950 and an interface 945. Examples of external storage medium 950 may include an external hard disk drive or an external optical drive, or an external magneto-optical drive.

Other examples of secondary memory 925 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 935 and communication interface 945, which allow software and data to be transferred from an external medium 950 to the system 905.

System 905 may include a communication interface 945. The communication interface 945 allows software and data to be transferred between system 905 and external devices (e.g. printers), networks, or information sources. For example, computer software or executable code may be transferred to system 905 from a network server via communication interface 945. Examples of communication interface 945 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 905 with a network or another computing device.

Communication interface 945 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 945 are generally in the form of electrical communication signals 960. These signals 960 are preferably provided to communication interface 945 via a communication channel 955. In one embodiment, the communication channel 955 may be a wired or wireless network, or any variety of other communication links. Communication channel 955 carries signals 960 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 920 and/or the secondary memory 925. Computer programs can also be received via communication interface 945 and stored in the main memory 920 and/or the secondary memory 925. Such computer programs, when executed, enable the system 905 to perform the various functions of the present invention as previously described.

In this description, the term "computer readable medium" is used to refer to any non-transitory computer readable storage media used to provide computer executable code (e.g., software and computer programs) to the system 905. Examples of these media include main memory 920, secondary memory 925 (including internal memory 930, removable medium 935, and external storage medium 950), and any peripheral device communicatively coupled with communication interface 945 (including a network information server or other network device). These non-transitory computer readable mediums are means for providing executable code, programming instructions, and software to the system 905.

In an embodiment that is implemented using software, the software may be stored on a computer readable medium and loaded into the system 905 by way of removable medium 935, I/O interface 940, or communication interface 945. In such an embodiment, the software is loaded into the system 905 in the form of electrical communication signals 960. The software, when executed by the processor 915, preferably causes the processor 915 to perform the inventive features and functions previously described herein.

In an embodiment, I/O interface 940 provides an interface between one or more components of system 905 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 905 also includes optional wireless communication components that facilitate wireless communication over a voice and over a data network. The wireless communication components comprise an antenna system 965, a radio system 970 and a baseband system 975. In the system 905, radio frequency (RF) signals are transmitted and received over the air by the antenna system 965 under the management of the radio system 970.

In one embodiment, the antenna system 965 may comprise one or more antennae and one or more multiplexors (not shown) that perform a switching function to provide the antenna system 965 with transmit and receive signal paths. In the receive path, received RF signals can be coupled from a multiplexor to a low noise amplifier (not shown) that amplifies the received RF signal and sends the amplified signal to the radio system 970.

In alternative embodiments, the radio system 970 may comprise one or more radios that are configured to communicate over various frequencies. In one embodiment, the radio system 970 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 970 to the baseband system 975.

If the received signal contains audio information, then baseband system 975 decodes the signal and converts it to an analog signal. Then the signal is amplified and sent to a speaker. The baseband system 975 also receives analog audio signals from a microphone. These analog audio signals are converted to digital signals and encoded by the baseband system 975. The baseband system 975 also codes the digital signals for transmission and generates a baseband transmit audio signal that is routed to the modulator portion of the radio system 970. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 965 where the signal is switched to the antenna port for transmission.

The baseband system 975 is also communicatively coupled with the processor 915. The central processing unit 915 has access to data storage areas 920 and 925. The central processing unit 915 is preferably configured to execute instructions (i.e., computer programs or software) that can be stored in the memory 920 or the secondary memory 925. Computer programs can also be received from the baseband processor 965 and stored in the data storage area 920 or in secondary memory 925, or executed upon receipt. Such computer programs, when executed, enable the system 905 to perform the various functions of the present invention as previously described. For example, data storage areas 920 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

Figure 10:
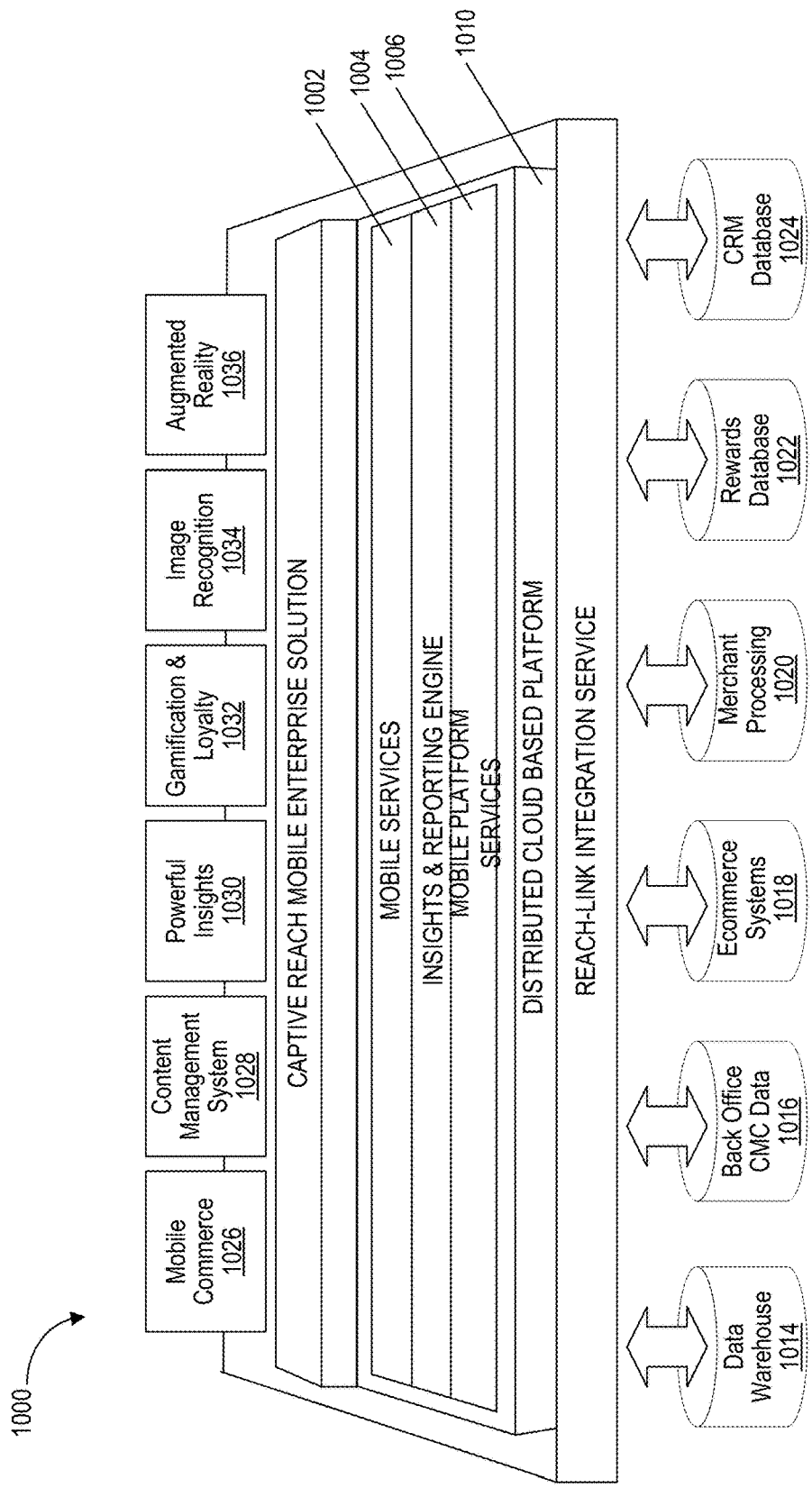
FIG. 10 is a block diagram illustrating a system for digital content and information sharing according to various embodiments.

FIG. 10 is a diagram illustrating a system 1000 for digital content and information sharing in accordance with one embodiment. At the core of system 1000 is, for example, a distributed cloud-based platform 1010 configured to provide services such as mobile service 1002, insights and reporting 1004, and mobile platform services 1006. These services can be integrated, via an integration service 1012, with resources such as a data warehouse 1014, a back office CMS module 1016, an e-commerce system 1018, a merchant processing module 1020, a rewards database 1022, and a CRM database 1024.

These services and resources can then be used to provide various applications to a business or user of system 1000. These applications include mobile ecommerce 1026, content management 1028, insights 1030, gamification and loyalty 1032, image recognition 1034 and augmented reality 1036. At least some of these applications are described in detail below.

Content Management System

The content management system module or application 1028 is a module built into the Captive Reach platform 1010 for distributing various types of content to one or multiple front-end mobile applications that are tied to Captive Reach 1010. In one example embodiment, there are nine primary types of content that can be distributed through the Captive Reach CMS module 1028, all of which will be described in detail in the following sections.

Content that is distributed to mobile applications through Captive Reach 1010 can be configured such that it is delivered according to a specific delivery schedule. Therefore, an organization can enter a date range, specific days of the week, specific hours of the day for each discrete piece of content to present itself on a user's front-end mobile application. Therefore, content can be pre-loaded into the CMS module 1028 in Captive Reach 1010 and will automatically display at the desired time of day or day of the week throughout a pre-defined range of dates.

Content loaded into the CMS module 1028 can also be segmented for delivery to a certain subset of application users based on a series of demographic or other requirements. For example: each application (e.g., 1026-1036) that is connected to Captive Reach 1010 can include a profile section for collecting demographic information from each of the front-end users. This information can be used to target and distribute content to users that match a specific demographic profile. Some examples of segmentation include: gender, age, ethnicity, religion, likes/interests, disease, treatment protocol, etc. Administrators of the Captive Reach platform 1010 can have the ability to predefine these demographic requirements for segmentation when setting up a piece of content for distribution. Users who have a profile that matches the demographic segmentation requirements will receive the content on their mobile device, and users who do not exactly match that particular profile will not receive that particular piece of content. Segmentation allows the administrator of the backend platform to run targeted content campaigns based on a very specific (or broad) set of demographic or other requirements, in order to increase the relevancy each piece of content has to the front end user.

Content loaded into the Captive Reach platform 1010 also has the ability to be targeted based on the position location of a user's mobile device. Each Captive Reach enabled mobile application utilizes location-based services to send a latitude-longitude location of each application user back to the platform 1010 for geographic segmentation. Geographic segmentation works by setting up what is called a geofence. A geofence is a pre-defined radius around a specific position-location that triggers the distribution of content to a front-end mobile application once the device's position location registers as being within the radius of the fence. Captive Reach 1010 holds a locations database, e.g., which can be part of the data warehouse 1014 that can be used for setting up a single or multiple geo-fences for a piece of content. The platform 1010 can be configured to log a user's position location every time a major location change is registered by the backend platform. If the user's location is within a predefined geofence that relates to an active piece of content, the user will then receive the content on their device. Otherwise, they will not. Geofencing ensures that location specific content is only delivered to users who are in a particular geographic region for which that content is relevant, and users who are outside of that area do not receive that particular piece of content. The types of content that can be shared through the CMS module can include advertisements, brands, events, information, galleries, news, offers, places and promotions.

Advertisements are a form of content that can be distributed via Captive Reach 1010 to a front end mobile application. Advertisements are typically a large banner-type advertisement that is visible on the home page, or some prominent page within the mobile application. The components of an advertisement can consist of a title, a URL or place within the app to direct the user upon click, and an image representing the advertisement. One or many advertisements can be loaded into the Captive Reach backend platform 1010, and will immediately present themselves on the mobile application. Administrators of the Captive Reach backend platform 1010 can have the ability to schedule, segment, and geofence each advertisement being run through Captive Reach 1010 in order to increase the relevancy of ads to the front-end users. Multiple advertisements sent to the same device may appear according to the order of the ads on the Captive Reach backend platform 1010, and may be scrollable via cover flow technology and swiping on the front-end mobile application.

Events are a form of content that can be created and configured through the Captive Reach backend platform 1010. This type of content pertains to a specific event that is happening on a specific date or throughout a date range. The components of event content include a title, description of the event, image(s), phone number (touch to call capabilities), start and end dates, and the specific location of the event. When event-type content is loaded into the backend platform, it will be associated with a specific category for this type of content. Events can also be scheduled, segmented, and geofenced according to an administrator's requirements and the event location. Additionally, event-type content has the ability to be shared through social media channels directly from the mobile application in order to increase the reach/exposure for a particular event. This is described in more detail below.

Administrators of Captive Reach 1010 can have the ability to incentivize users to share event content by awarding a point total to the user for doing so. This loyalty type feature can be custom configured on the backend platform on a per event basis, and can be changed at any time. Sharing can also be disabled for a particular event if the administrator of Captive Reach would like to keep the recipient list exclusive.

Information can be another type of general content that can be created and distributed by the Captive Reach backend platform 1010. Information content is simply general informative or educational content that the Captive Reach administrator would like to push to the applications in their user universe. Information content contains a title, image(s), and a general description for the piece of content. This type of content can also be scheduled, segmented, and geofenced based on a predefined set of parameters. Additionally, information content has sharing and loyalty associated with it, so point totals can be assigned to the content as an incentive for users to share content. Information content is assigned to a category and when a change in made on the backend, it will immediately be reflected in all front-end mobile applications to which that particular piece of content was distributed.

The backend platform 1010 can allow for the creation and distribution of image galleries down to mobile applications from the backend platform 1010. An image gallery module (not shown) can be included within the CNS module 1028, or as a standalone module, and can allow the administrator to upload a series of images that are to be displayed in an image gallery category on the front-end mobile app. The platform 1010 can support multiple image capabilities. In certain embodiments, the users interact with images on the device by using coverflow technology, which allows them to swipe through the various images available. Images loaded through the platform can be geo-fenced, demographically segmented, and scheduled prior to distribution.

The news section (not shown) of the backend platform 1010 allows the administrator to upload news based articles to the platform 1010 and have those pushed to the front-end mobile application in real time. News follows the same format as other content areas in the CMS module 1028 containing a title, body text, external link option, and social sharing aspects. Any news article can be geo-fenced, segmented demographically, and scheduled for delivery.

Offers are another form of content that can be distributed via the content management system module 1028. Offer type content is designed to host a deal for a particular good or service. It contains all of the same content fields as other content types run through the CMS module 1028. However it can allow the administrator to input a dollar value amount, an original price amount, and when the content renders on the front-end, it automatically calculates a savings percentage for the end user. Offers run through the CMS module 1028 can also be redeemed by the user, such that they cannot re-use or recycle offers. Redemption is done through the entry of a redemption code that reconciles with the backend platform 1010 and either allows the user to successfully redeem the offer or not. The number of redemptions allowed, either per user or per offer, can be configured through the backend platform 1010. Once a user reaches their maximum number of redemptions, they can no longer see the redemption option on the offer detail page.

The Insights Module

The insights module 1030 of the Captive Reach platform 1010 allows administrators to see reports on application usage across the entire user universe. Insights come in several forms and focus on reports detailing, for example: how users are engaging with content, most popular content on the app, where users are when they are viewing content, what social channels users are sharing through, and other custom defined reports based on the features and functionality of the front-end application(s). Insights can be powered by an "events" architecture that is built into every Captive Reach powered mobile application. The events architecture works by sending an API call to the Captive Reach platform 1010 each time a pre-defined event or action occurs on the mobile device. Using this architecture, a front-end mobile application can be setup to send an event every time a specific page is viewed, button is clicked, etc. When going through the Captive Reach mobile integration process, events can be defined during the requirements phase of the project cycle. These specific events are then integrated into the mobile application code for each application developed, and reports on the backend are built off of all events that are tracked and logged.

The following are specific insights reports that can be available through the Captive Reach platform 1010: Content Insights; Market Based Insights; Consumer or user Insights; Target Insights, Geographic Insights; Patient Insights, Site or Clinical Insights, and Social Insights. At least some of these are described in more detail below.

Content Insights are reports based on the events architecture that track a particular event on the mobile application related to content views. These reports are sourced based on the types of content pushed to a mobile application that come out of the content management system module 1028. Reports can be sorted and filtered based on the type of event being tracked, and can also be broken down by date range.

Consumer or user insights show a roll up of user activity on the mobile application broken down by month. The top level summary shows the number of active applications during a particular month, along with the number of times the application was opened, number of items shared through social media, the number of offers redeemed, the number of push notification alerts received, the total number of points awarded to users, etc. Administrators of the backend platform 1010 can select a particular month and be presented with a breakdown of all active users who used the application within that given month, along with their top-level statistics around opens, shares, redemptions, push notifications, total points awarded, etc. The administrator can delve in one layer deeper by clicking on an individual user's name in order to see a detailed user profile with their activity of application usage. The user profile shows the basic demographic information collected for that user, their last known location, along with their summary statistics around what content they have viewed and engaged with on the mobile application.

The Target Insights are an important set of algorithms, e.g. based on market verticals that can, for example, be defined as: Hospitality, Convenience Stores, General Retail, Restaurants, and Gaming and Casinos. For other type of applications, other types of articles or classifications can be defined.

The algorithms developed are intended to locate a device, identify when that device is in a target location, associate that target location with an algorithm, and define based on the target location, target vertical, or classification and the associated algorithm, if that device should be captured and if so, what elements of the device should be captured within the platform 1010 and reported.

For example, in the hospitality space, the system 1000 can be set up to determine when the user is at or near the client's locations as well as when the user is at or near a competitor. Other information such as how long was the user at or near the client's locations, how long the user is at or near a competitor's location, etc. Thus, for example, if the system 1000 determines that a user is nearing the client's location, then the client's application built on platform 1010 can be configured to message the user with a limited time offer or promotion. Moreover, and maybe more importantly, when it is determined that user is near a competitor's location, the same type of offers can, for example, be pushed to the user's device.

For example, in the Clinical Research space, the system 1000 can be set up to determine when a research patient or researcher is at or near a clinical locations as well as when the research patient or researcher is at or near their home or other location of interest loaded into the platform 1010. Other information such as how long was the research patient or researcher at or near the clinical locations, how long the research patient or researcher is at or near a home location or other location of interest, etc. Further information such as how long. Thus, for example, if the system 1000 determines that a research patient or researcher is nearing the clinical location, then the clinical research application built on platform 1010 can be configured to message the research patient or researcher with actionable content. Moreover, in one exemplary embodiment, when it is determined that research patient or researcher is near a target location, the same type of message, for example, be pushed to the research patient or researcher device.

This type of information can also be used to allow the Clinical Coordinator to determine how much time the research patient or researcher are spending at or near their locations as well as how long they are spending at or near another target location, and to compare the two or run other analytics on this information. An example Pseudocode Algorithm for Hospitality industry is included in U.S. patent application Ser. No. 14/738,766, entitled "System and methods for managing and conducting clinical or other research using a digital content and information sharing system" filed on Jun. 12, 2015, which is incorporated herein by reference.

An organization or individual can upload a list of target locations and associate each location with an industry vertical. Once an industry vertical or a classification is associated with a location, a rules-based algorithm will be associated with each location. As location-aware devices send event-based updates to the mobile platform 1010, each device will be run through the rules-based algorithm, and if the algorithm variable USER_LOC results in a positive result, event-based data will be captured from the handset and stored in a database or flat-file structure within the mobile platform 1010 for future analytics and reporting.

In this way, when a location-based device is located on or near a predetermined location uploaded by a client. The method will allow a user to perform the following tasks mainly to upload target locations and define which vertical those locations are associated with, and report on when location based devices are on or near target locations.

Geographic insights relate to the physical geographic disbursement of users throughout the world. Users can be shown on a map viewfinder based on their concentrations in various geographic areas across the globe. Administrators have the ability to click on a particular concentration of users and be taken to a close-up view of that geographic region, showing in more detail where the application users are located. Administrators have the ability to filter the results shown on the map based on various demographic profile components (age, gender, etc.) and/or device type.

Social Insights show detailed reports on how users are engaging with social media from within the mobile application. By default, this report displays how many items have been shared through social media in any given month, along with the specific social media channel that content was shared through (i.e. Facebook, Twitter, LinkedIn). Administrators have the ability to focus on a particular month and see a breakdown of all of the users who have engaged with social media that month, along with their individual sharing behavior.

The Captive Reach mobile platform can have a built-in gamification module 1032 that enables the use of game mechanics, progress tracking, and rewards distribution all through a central platform 1010, without the use of disparate systems. The gamification module 1032 of the mobile platform will be used to power the rewards points system for all Captive Reach enabled mobile applications.

All mobile platform enabled mobile applications can be enabled with API linkages to Facebook, Twitter, and LinkedIn on the end-user side. Users have the ability to connect to these social networks for the purpose of sharing content on the mobile application with their respective social networks. Sharing can be enabled or disabled for any piece of content on the mobile application through configuration on the mobile platform. When sharing is enabled, front-end application users can, e.g., see a button or icon to share that particular piece of content. When the user selects the sharing option, they can be presented with the various networks through which the content can be shared. In order to incentivize users to share content through social media, content can be assigned a point value. When a user shares content, they can then be rewarded the corresponding point value.

In order to power the distribution of rewards for application behavior, each platform enabled application uses an "events architecture." Events architecture is a simple API call that is made to the mobile platform server when a specific action or "event" occurs on the mobile application. A list of actions or triggers to make a platform call are defined during the requirements definition phase of the project cycle, and will serve as the basis for users to accumulate points, advance the progress of the user's profile, and/or be rewarded for completing tasks. Events on the mobile application will be classified according to their business objective value (i.e. progress through the app, consuming application content, etc.), and a corresponding point value will be assigned to that particular event.

Events can be assigned to any application action, combination of actions, timeliness of actions, or repetition of actions. The structure of events reporting to the platform 1010 can be defined in the requirements definition phase of the project, and will serve as a blueprint for implementing the rewards structure into the application.

As users interact with the application, consume various pieces of content, share content to social media, participate in fitness activities, etc. they will accumulate points on the Captive Reach platform. Points are used as a system of accounting for rewarding users for certain behaviors. The method of providing rewards to the user will be through the use of a digital profile that is representative of their progress and usage of the mobile application. As users frequently utilize the various features and functionality of the application, they will be rewarded with medals, badges and points that can be redeemed for various items. As mentioned previously, points can be used as a system of record for applying these rewards to a user's avatar, such that once a certain point threshold is met, the user's avatar will automatically upgrade.

The primary areas of the application, which will be enabled with the events based architecture, include but are not limited to: Social Media sharing; Consuming recent application content; Percentage of the application used; Percentage completion of mobile app; Consumption of specific application content; Regular usage of the application; and Consuming news and information.

Reach Link 1012 can be an API layer built into Captive Reach 1010 for the purpose of integrating with already existing data systems. Reach link 1012 serves as a layer in the platform to both integrate already existing APIs for the sake of enabling some new functionality on the mobile application, by using the Captive Reach platform 1010 as a conduit. Also, reach link is used for the sake of ingesting content into the CMS module 1028 through a feed, which eliminates the need for manual updates to the CMS in order to ensure that fresh and relevant content is being pushed to the mobile application. Reach Link 1012 can therefore be a crucial piece of the Captive Reach platform 1010, as it allows for the integration of already existing systems into the front-end mobile applications being built off of Captive Reach 1010.

The portal section can be included in platform 1010 to allow an administrator to change the default logo on the backend platform 1010. This is done to allow the client or organization to easily customize the platform 1010 according to their logo and style guidelines. Additionally, the portal section of the backend platform 1010 can be configured to allow the administrator to select time zones for scheduling content on the mobile application to ensure that content is delivered at the correct time to the front-end users.

A modules section can be included in platform 1010 to allow an administrator of Captive Reach 1010 to toggle the various modules on the backend platform 1010 on or off depending on their business needs the functionality of the front-end mobile application. The platform 1010 can be built in a playbook architecture, which allows for easy configuration of features and modules on a per client basis with no extra development efforts.

A users section can be included in platform 1010 to allow an administrator to add both new admin and child users to the platform 1010. Users are configured to have various access rights to the platform 1010 including full administrator rights, or limited rights according to access to various modules or geographic regions for content distribution.

A locations section can be included in platform 1010 to allow an administrator to populate the internal locations database with new places for the sake of geofencing content being run through the Captive Reach platform 1010. This section can house all of the locations used for geo-fencing, and can be added to, subtracted from, or updated at any time without the need to utilize development talent to make these changes.

A categories section can be included in platform 1010 to allow an administrator to actually add, subtract, or rearrange the categories on the front-end user interface of the mobile application. Also, category icons can be assigned to a particular module of the platform 1010 in order to enable a particular function on the front-end mobile application. By having dynamic categories on the back-end platform 1010, the administrator has the ability to manipulate the application's front-end user interface dynamically, without having to do additional development, or make a new submission to the respective application marketplaces. This is particularly valuable when the need arises to add a new section to the application for content distribution on the fly.

Figure 8:
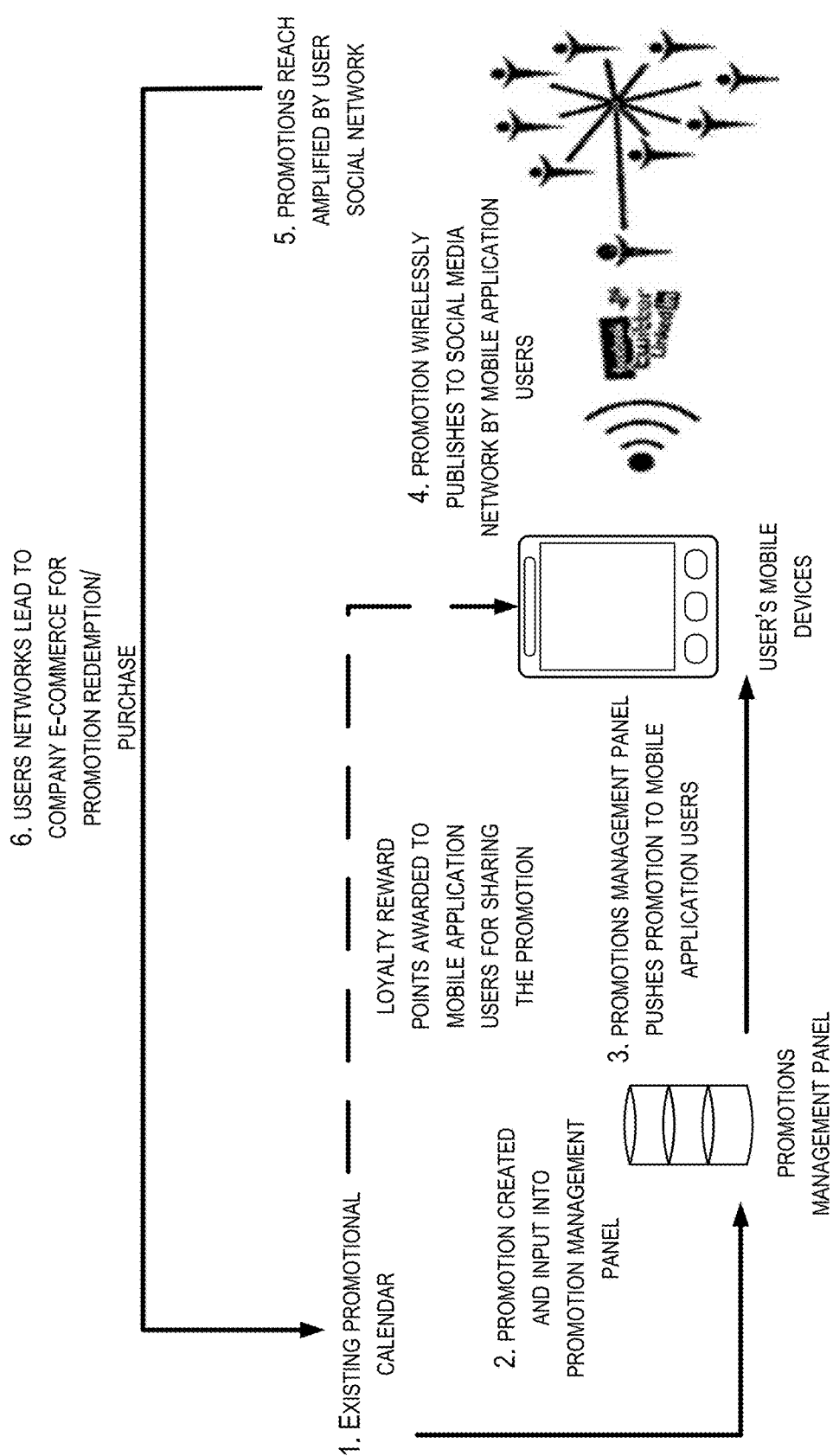
FIG. 8 is a block diagram illustrating a platform according to various embodiments.

As noted above, system 1000 can be used to provide users with incentives to share offers and content, e.g., via their social media accounts. FIG. 8 is a block diagram illustrating the platform 1000 according to various embodiments. Management panel, configured to run on platform 1010 can be configured to, for example, push promotions to a plurality of user devices. As noted above, a mobile application can first be downloaded, for example, to mobile operating systems, tablets, PCs, Macs, and other operating systems alike. The application allows users to receive digital content from a central backend platform 1010 that can, for example, be built as a Software-as-a-Service (SaaS) platform.

The operating party, e.g., brand, client, business, etc., of the SaaS platform 1010 can then be provided with the ability to upload digital content into the platform that can be pushed to all users who have downloaded the application.

Users of the application can have the option to customize the content that they receive from the platform 1010 and push it to their Social Media network(s) 204. Some typical types of digital content that can be pushed to Social Media include but are not limited to, promotions, text-based messages, images, audio and videos.

Users are provided an incentive to share this content to their Social Media assets. Such incentives include but are not limited to loyalty points, rewards points, discounts on products, coupons, memberships and giveaways. When digital content is shared to the application user's Social Media platform, the incentive is then awarded to that user through the Promotions Management Panel 200.

The intent of sharing digital content to Social Media is to utilize the user's existing Social Media network to gain exposure for that digital content. In the case of a business utilizing this software, a user would share information or a promotion for a specific product or company initiative, and members of the user's Social Media network would then be exposed to that content resulting in an impression as in traditional advertising. The more members of the user's Social Media community that engage with the digital content that is shared to the user's Social Media assets, the greater the exposure given to that piece of digital content, and the higher the likelihood that the content goes "viral." An example of this software platform as executed for a company running a promotion through user's mobile platforms is illustrated in FIG. 2. In this example, the incentive for users to share the digital content is the awarding of loyalty rewards points.

It is worth mentioning that this application provides businesses, organizations, agencies and individual users a method of promoting a piece of digital content through leveraging an existing Social Media community as a conduit for sharing that piece of content The software does this by providing a back end SaaS platform 1010 for the primary user of the software to input the digital content that they wish to share through Social Media, it provides a mechanism to reach people present in the existing Social Media community to receive that content through the use and download of an application that can be either on a mobile device, a tablet device or downloaded to a browser. The application provides the application users with a channel to share that content to their individual Social Media Networks. The application also provides its users incentives for sharing a piece of content to their Social Media networks by giving them rewards for each piece of content shared.

The software platform 1010 offers the central user an entire backend system that provides reports and analytics on number of application opens, content views and content shares. This allows the central user to directly view the effectiveness and response levels to each piece of digital content that is uploaded into the Promotions Management Panel 200. The Promotions Management Panel also offers a number of customizable features which allow the central user to differ the look and feel of the digital content that they are uploading into the Promotions Management Panel 200, determine the incentive awarded for sharing of the digital content and duration of time with which digital content can be shared.

Research Conducted Using Target Insights

In various embodiments, target insights are collected and applied during research (e.g., clinical trials) that include multiple participants (e.g., patients). For example, in various embodiments, target insights with respect to one or more research participants can be collected via client applications installed on participants' mobile personal devices (e.g., smartphone, tablet PC) and/or wearable technology (e.g., smartwatch).

In various embodiments, client applications can be configured to collect and transmit real time data (e.g., event, time, geolocation, social media, case report forms, patient reported outcomes, adverse events, and other patient reported or doctor reported data) to the cloud-based mobile platform 1010. For example, a participant in a study may upload data that includes, for example, but not limited to, audio, still images and photographs, video, and/or text. Additionally, the mobile platform 1010 may collect, receive, and store other relevant data with respect to individual research participants or others associated with Research including, for example, but not limited to, demographics, browsing history, visits, patient reported outcomes, adverse events, medication adherence, and mobile directly observed therapies.

According to one exemplary embodiment, the mobile platform 1010 can receive one type of data from a research participant's client application. The data from the research participant can indicate the research participant's status with respect to a target location. In various embodiments, the data from the research participant can further include, for example, but not limited to, adverse event reporting and verification, and other compliance based information such as patient reported outcomes, adverse events, medication adherence, and mobile directly observed therapies. For example, the data may be geolocation data indicating that the participant in a weight loss study is near or at a Research Clinic. Alternately or in addition, the data received from the research participant can be social media data confirming that the research participant has checked into an approved doctor's office or clinic. The data received from the research participant can also include audio and/or visual (e.g., video, photograph) confirmation of the event.

In response to the data received from the research participant, the mobile platform 1010 can select one or more types of data. In various embodiments, the mobile platform 1010 can determine to transmit data to the research participant and/or a research organizer. According to one exemplary embodiment, the mobile platform 1010 can select a second type of data based on data received from the research participant including the status of the research participant with respect to a target location (e.g., restaurant, clinic, fitness center). Additionally, the mobile platform 1010 may select the second type of data based on attributes associated with the research participants (e.g., demographics, timelines, language, ethnicity, etc.). The second type of data may include, for example, but not limited to, alerts, surveys, and other contextual messaging. For example, in response to geolocation and/or social media data indicating that the participant in a Research study is at or near a clinic or other Target, the mobile platform 1010 can select and transmit data to the research participant that includes alerts, surveys, and other contextual messaging. In addition, the mobile platform 1010 can also select and transmit data to the research organizer alerting the research organizer to an adverse event and/or non-compliance with one or more requirements associated with the research.

According to one exemplary embodiment, the mobile platform 1010 can analyze data received from a plurality of research participants to generate one or more reports. Furthermore, the mobile platform 1010 can associate data received from each research participants and reports associated with or are relevant to each research participant. The mobile platform 110 can store records (e.g., patient records) associated with each research participant as well as sites, coordinators, or other relevant persons, locations or items. In various embodiments, data from research participants may be analyzed in real time. Furthermore, the data and/or the reports may be stored at the mobile platform 110, and be made available to research organizers and other relevant parties.

Figure 11:
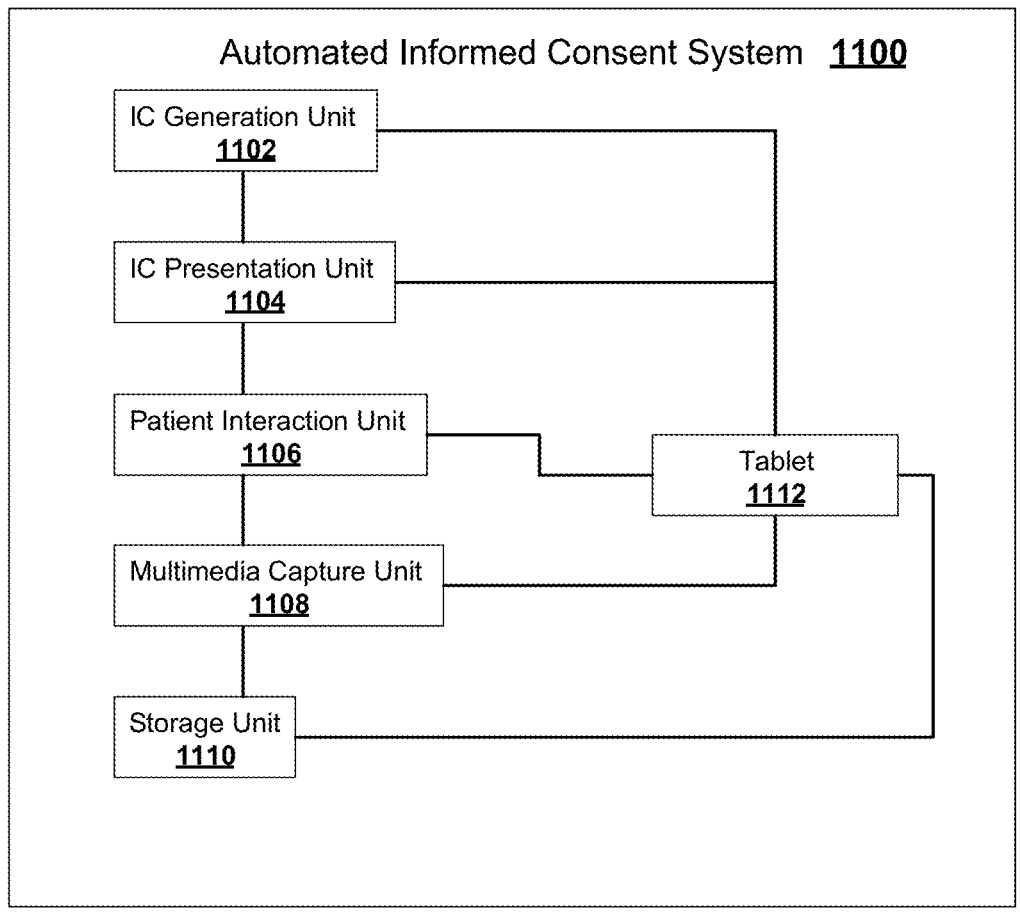
FIG. 11 illustrates a system for obtaining informed consent from a patient, according to one embodiment.
Figure 12:
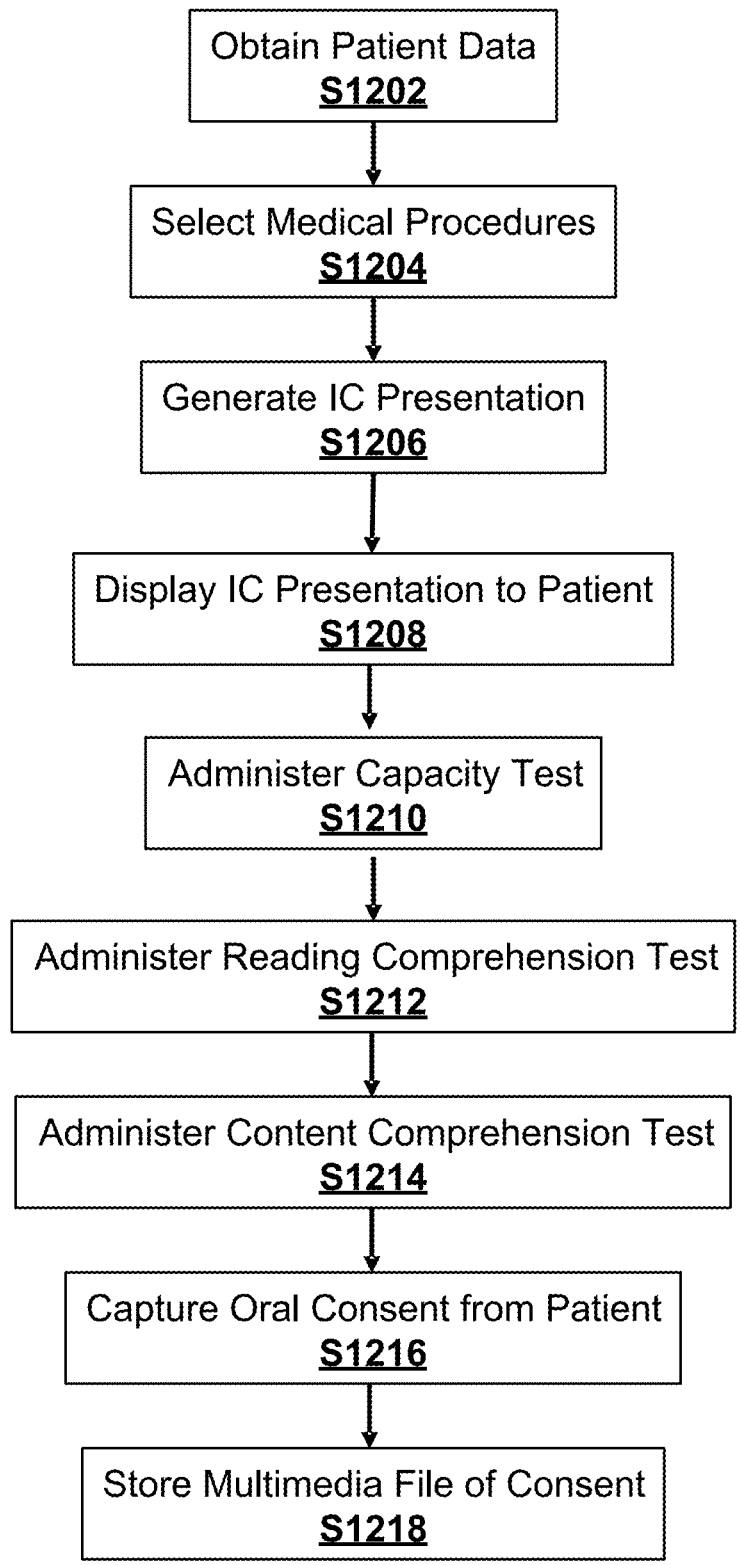
FIG. 12 illustrates a method for obtaining informed consent from a patient, according to one embodiment.

FIGS. 11-12 and the corresponding description of co-pending U.S. patent application Ser. No. 13/487,155, entitled "Systems and methods for automated informed consent" filed on Jun. 1, 2012, which is incorporated herein by reference as if set forth.

Embodiments incorporated herein provide for systems and methods for an automated informed consent process using a customized, interactive, multimedia informed consent presentation. The informed consent presentation establishes bona fide patient informed consent (IC) that educates and empowers the patient while protecting the medical provider according to all governing regulatory bodies, and brings clarity to these concepts through visual and auditory explanations. The system can prove to a legal certainty that the patient was competent and comprehended the IC.

In one embodiment, the informed consent presentation is a multi-media consent process that engages the patient in an educational experience in his or her own language to guide the patient through the educational process of informed consent prior to undergoing medical treatment or enrolling in a clinical trial. The informed consent application may be configured to: deliver all information needed for IC in a consist interactive multimedia form that is documented accurately; give oral and graphical description of procedure, risks, and options available; contain a quiz with patients responses to confirm comprehension; create a valid legal document stored on a electronic medical record; and review all up-to-date legal mandates for IC, including all options that must be discussed with the patient, both mainstream and complementary procedures available.

The systems and methods described also provide protected identity verification, time stamps, and embedded quizzes to determine patient capacity to consent and test patient knowledge and understanding of the medical procedure and associated risks. Thus, as opposed to paper consent, patients are properly informed and educated, are more likely to be proactive and involved in their own medical care, be more satisfied and with better health outcomes. The automated informed consent process improves operational efficiency, drives patients to customers, and provides improved health outcomes at a lower cost. This saves time and money The informed consent process is a modular, multilingual, multimedia and personalized informed consent application that will bring clarity to concepts through visual and auditory explanations while also verifying, documenting and time stamping the patient's legal capacity, identity and consent certification. The patients are progressively quizzed during the informed consent presentation to ensure their understanding, and must answer a predetermined number of questions correctly before they are permitted to consent to a medical procedure or enroll in a given clinical trial for medical procedure or treatment. Embodiments may also include voice recognition that allows for those with physical impairments to use the system, too. The informed consent presentation is customized for each patient through seamless interoperability with electronic health records (EHR), electronic medical record (EMR) and personal health records (PHR). The informed consent presentation is applicable for all medical providers mandated to obtain patient consent for treatment.

Improved patient compliance, safety, and outcomes is the result of prepared patients who know what to expect and can ask questions with quality and verifiable patient understanding well before the day of the procedure. Standardized, consistent patient education that is procedure and patient specific conducted a computer or tablet device will improve patient education, understanding, and compliance. Reduced liability exposure for physicians, hospitals, and clinical trial sponsors will be the result of an informed consent process that is standardized, unbiased, recorded, time-stamped, and reviewable for the protection of both the patient and the medical provider or clinical trial sponsor. The value delivered to the customer is the paradoxical ability for physicians to spend less time with each patient on the informed consent process while at the same time improving patient education and the doctor-patient communication resulting in educated, empowered, satisfied, and compliant patients.

In one embodiment, a patient-centric application may be provided that will educate the patients and streamline the entire informed consent process for medical procedures, screenings, and clinical trial enrollment.

The initial system may comprise a plurality of application modules that allow a doctor, or hospital to quickly and easily assemble an automated consent program for a specific procedure. Some of these modules will be generic, i.e., patient information, introduction, explanation of the consent process, etc., and some will specific to the procedure or trial. Once the modules are assembled and the application is built, it can be loaded onto a mobile device, such as a tablet. When the patient arrives for a procedure they can be given the tablet, which will walk them through the consent process.

The application may be a series of videos and pictures, preferably with voice overlays explaining what is going to happen, the patients options, risks, etc. While text can be included, it is generally avoided because people are less likely to read and understand text, and it is easier to build multiple language versions by swapping out the audio files.

At various points in the process, a test can be given to the patient, i.e., a few short multiple choice questions, designed to confirm that the patient understood the content. If a patient fails a test, the content can be replayed, new, more in depth information can be provided, etc. If a patient continues to "fail" the test, a nurse or doctor can be summoned to help clear up any questions.

The test may change the second time, i.e., instead of multiple choice, it may require an answer be spoken or typed in, the questions may change, etc., in order to ensure the patient is really comprehending.

Each application can also have a set of thresholds in terms of how many right answers or the minimum knowledge that is required to move on.

Once the patient has reviewed all the information, passed the required test, etc., they can provide consent, which can be recorded. For example, the patient may speak their consent, which can be captured via both video and audio recording through the camera and microphone included in the tablet; a digital signature or electronic signature pad can be used; or the patient may speak their consent and then sign a paper form, but the consent will also have been recorded.

Importantly, the consent is not necessarily just a signature or acknowledgement: rather it can be interactive requiring them to restate certain key information in response to a question, queue, prod, etc., or at least listen to key information and provide acknowledgement. In general, what is required for "consent" can be designed to include and verify all of the factors necessary to prove consent in a court of law, which are identity, capacity, and comprehension. A time stamp can also be included.

In addition, the camera included in the tablet can be used to record and analyze the patients behavior, capacity, awareness, etc., in order to ensure the patient is capable of providing consent. If it appears that a problem exists, a nurse or doctor can be summoned to further evaluate the patient.

As a result, there is a clear record that the patient received the information, understood it, and consented.

The patient can be quizzed with respect to their education, mood, autonomy, i.e., desire to know about health data, language, and reading level, and their comprehension can be tiered accordingly, but so as to ensure that a legal consent is obtained. Moreover, a patient can be requested to provide consent and other information above and beyond what would normally be obtained, in order to recruit them for clinical trials later on.

In general, the consent data, i.e., all the information gathered during the process can be stored in a database. With the added information, the patient data can be filtered based on the needs of a particular trial in order to identify potential candidates. In certain embodiments, all of the data is stored in a cloud based storage system.

Ultimately, the storage system can be linked to electronic health records, which can enable a host of additional services.

One embodiment of a system for automating informed consent is illustrated in FIG. 11. An IC Generation Unit 1102 is used to generate an informed consent presentation, based on the procedures that the patient will be undergoing, the patient's medical history and any other factors that the person creating the presentation decides to include. Next, an IC Presentation Unit 1104 transmits the presentation to a computer, such as a tablet 1112, for displaying to the patient. The computer may be any type of computing device— portable or otherwise—as long as it includes a processor, memory and a display screen to display the informed consent presentation to the patient. The computer also needs an audio capture device, such as a microphone, to capture the audio of the user providing consent, or an image capture device, such as a camera, to capture the video of the user providing consent. If the computer is a tablet 1112, the display screen of the tablet (not shown) may also be the input device where the patient provides input. If the computer is a more traditional desktop or laptop computer, a separate input device, such as a keyboard, mouse or physical input buttons may be used.

During the presentation of the informed consent presentation to the patient, the patient interaction unit 1106 coordinates patient interaction with the tablet 1112 in response to questions or instructions during the presentation. This includes responses to a mental capacity test, a reading comprehension test, a content comprehension test and any other interactions or feedback that the patient provides during the presentation.

In one embodiment, at some point during or at the end of the informed consent presentation, the patient may be requested to provide their oral consent by stating that they consent to a particular procedure that they agree to enroll in a particular clinical trial program, or some other statement relevant to providing consent. A multimedia capture unit 1108 will coordinate the capture of the patient's oral consent using the audio or video (or both audio and video) captured by the tablet 1112. Once the audio or video is captured, the storage unit 1110 will store a resulting multimedia file in a database (not shown) for later access. The file may be a known multimedia file for any type of audio or video, or the file may be stored in a particular format required for protected medical data, such as HL7.

One embodiment of a method of capturing informed consent from a patient is illustrated in FIG. 12. In one step S1202, patient data is obtained from a patient's medical records, genomic data, patient input, etc. In step S1204, at least one medical procedure or clinical trial is selected by a health care professional. Next, in step S1206, an informed consent presentation is generated based on the selected medical procedures and the patient data. For example, if the patient medical data indicates that the patient has a particular medical condition which increases the risk of the selected medical procedures or clinical trial, the informed consent presentation will be amended to tell the user of this increased risk. The informed consent presentation may also be amended in real time during the presentation to the patient if the patient provides new medical information which affects the risk of the selected procedures.

In step S1208, the informed consent presentation is displayed to the patient on a display screen of a computing device, such as a tablet, phone, laptop or desktop computing device. As part of the overall informed consent presentation, the patient may be given a capacity test S1210 to measure their mental ability to provide consent, a reading comprehension test S1212 to determine the patients ability to understand the medical language used in the presentation, and a content comprehension test S1214 to determine whether the patient understood the information provided on the medical procedure, the risks involved, and the implications of their consent to the procedure.

The patient will then be asked to provide an oral statement of their consent to the medical procedure and any other statement of understanding that may be necessary. In step S1216, this oral statement is captured by the tablet or computing device using a microphone or camera, and the resulting multimedia file is then stored (step S1218) as part of the patient's overall consent files.

In addition to the patients oral statement, the patient may also provide an electronic written consent by digitally or biometrically signing a form on the display screen, by typing their initials or name in a particular box, or providing some other type of written authorization that can be stored in another type of file.

Capturing Patient Consent

In one embodiment, the consent process is recorded, reviewable, and archived to assure regulatory compliance for clinical trial sponsors and medical providers according to all governing regulation.

In the systems and methods described herein, an application such as that running on a tablet computer is provided to bring together digitized IC, mobile patient education, and secure health care access. In one embodiment, the system for automated informed consent is a cloud-based interactive multimedia application which is executed on a tablet, mobile phone or other portable media device connected to a network by a network cable or wirelessly. The system may also be run as a web-based application where the patient can access and interact with the presentation from any computer connected to a network. The tablet or computer running the informed consent application may include a camera or microphone so that the user's consent may be captured on video or audio (or both) and stored. The video and audio will provide additional evidence of the user's consent by recording their voice intonations, eye movement, and overall behavior. The patient may be asked to recite specific sections during the capture of the video or audio which pertain to their actual consent to the procedure or acknowledgement of a particular high risk. The video or audio file may be time-stamped as well. The patients answers and recorded consent may be stored remotely on a central server or cloud, both for security of the data and to avoid loss of data stored on the computer running the application.

The format of the captured audio and video may be in HL7 (Health Level 7) compliant formats, although it may be separate from a more traditional informed consent file, which is typically stored in a portable document file (PDF) format.

Obtaining Patient Information

The patient may be tested to determine their educational level, mood, autonomy (desire to learn about the procedure or clinical trial), language and reading level, etc. The minimum thresholds required for consent may be raised or lowered depending on this information. In addition, providing a patient with options to learn more about a procedure during the presentation will also increase the patients overall comfort with the procedure. Information on the patient's mood may be provided to the doctor who is performing the procedure in order to alert them that the patient is apprehensive or may need further counseling regarding the procedure.

By obtaining information about the user's comprehension and overall capabilities, the patients can be "tiered" into predetermined levels so that the informed consent presentation is customized for the tier that the patient falls into. The informed consent presentation may also provide options for patients to obtain more information about a procedure, alternatives and risks if the user wants to know more. Even specific details such as the history and experience of the physician performing the procedure, the length of the procedure, environment in the procedure room, etc. may be provided. The additional details may put some patients at ease if they know more about the experience before going in.

In one embodiment, the informed consent process would consist of a very simple "patient check-in" process without the need for billing/insurance checks—just the basic demographic info for the patient, with their address and any other info needed to pay the patient (address, social security number, W9, etc). It would have audio/video recording of patient consent with some simple guidance, administer quizzes of the content, and provide the ability for the patient to flag confusing info that they want to review before consent with the health care provider.

In one embodiment, the patient may provide additional information that can be used for future evaluations of the procedure and options for other medical treatments, including enrollment in clinical trials. The patient may complete an overall health profile, enter geographic and demographic information and other information that may be used to offer the patient new treatments, medications or opportunities for clinical trials. The patient information is then stored in a database where it can be accessed by the physician, a health care provider or company that is looking for patients that may benefit from new treatments, drugs or clinical trial testing.

In another embodiment, the patients medical records, including the EMR, EHR and PMR may be obtained and used to customize the informed consent presentation. This may include their genomic data as well. For example, certain procedures may be more risky for patients with certain conditions, so the presentation may be customized to explain this heightened risk to the patient if their records indicate they have another condition or if they indicate that they have a certain condition during the informed consent process. Furthermore, their medical record data may be stored in the overall consent database for future access by the physician, health care provider or company looking for patients for new treatments, drugs or clinical trials.

Modular Informed Consent

The informed consent system may be modular, in that separate informed consent presentations may be created for each medical procedure, clinical trial or other component of informed consent. In one embodiment, when the procedures that a patient will be undergoing is entered into a medical software system, the unique code (CPT, for example) or procedure selected may automatically trigger the creation of the informed consent presentation with presentations corresponding to each code or procedure selected. Other modules, such as a capacity evaluation module (described below) may also be included in the overall presentation. Each module selected may then be integrated into a single presentation that is given to the patient.

Capacity Evaluation

In one embodiment, one portion of the informed consent presentation is a capacity evaluation test that determines whether the patient possesses the mental capacity to make an informed consent decision. Physicians often ask patients to make complex choices about diagnostic studies or treatments. Medical decision-making capacity includes a patient's ability to understand relevant information and appreciate the consequences of a decision. Clinicians often do not assess and lack formal training in assessing patients' capacity. As a result, clinicians regularly fail to identify patients who are incapable of informed decision-making, despite the prerequisite of capacity for valid informed consent. Researchers reviewed more than 40 high-quality prospective studies of inpatients, outpatients, and healthy controls in which medical decision-making capacity was evaluated with various instruments; patients with severe psychiatric illness were excluded. Incapacity (as judged by a gold standard of forensic or expert psychiatric evaluation) was common in medical inpatients (26%), and physicians missed identifying patients with incapacity 58% of the time. In one embodiment, the ACE Capacity Evaluation Tool may be included in the informed consent presentation to evaluate a patient's actual decisions, which unlike other instruments focuses on unrelated clinical vignettes.

The patient may also be evaluated to establish a reading comprehension level to adjust the informed consent presentation to that patient's reading level and ensure complete understanding of the medical procedure. The patient may be asked what their educational level is, or they may be given a series of reading comprehension-like questions to evaluate their reading comprehension level indirectly.

Comprehension

In one embodiment, the patients comprehension of the informed consent presentation is measured to ensure that the patient understood the material and remembers important aspects. By the use of a modular learning management system (LMS) with interactive quizzes, repeat back questioning and scored performance, the medical provider and trial sponsors can be assured that the patients have full knowledge of what their diagnosis is, why they are enrolling in a trial or having a procedure done, the alternatives available and the risks of the trial or procedure, including the options of not-participating in the trial or not having the procedure/treatment.

The patient may also be evaluated during the informed consent process to determine their level of understanding and comprehension. Many informed consent papers use highly-technical medical health language, and it may be necessary to provide additional explanations of these terms or ask the user if they understand all of the terms. In one embodiment, certain words may be linked with definitions or further explanations that the user can view by clicking on the word or some annotation near the word.

The patient may be provided with periodic questions during the informed consent presentation which ask about the presentation. The level of aptitude for each patient may be customized by the presentation creator and may depend on each procedure, in which case the patient may not need to answer every question correctly. If the patient doesn't meet a certain level of aptitude by answering a certain threshold amount of questions correctly, the user may be asked to watch a portion of the presentation again. If the patient still does not answer the questions correctly after a second iteration, the presentation may flag the question or section of the presentation for a physician or other health care provider to follow up on directly with the patient to ensure understanding.

If the patient is viewing an informed consent presentation related to a clinical trial, the patient may be asked questions relating to their demographics (to confirm eligibility and availability), be provided with a high-level description of the trial and asked to consent to participation in the trial and use of their medical data obtained during the trial by the company managing the trial, a public health agency or other regulatory body. In one embodiment, the patient may be asked to provide their genomic data.

Clinical Trial Recruitment Process

In one embodiment, patient medical data from the patient's medical records or information provided by the patient during the informed consent process may be used for a clinical trial recruitment system. The medical data may be stored in a database which can be searched by a company running a clinical trial to identify potential candidates for participation in the clinical trial.

The overall clinical trial recruitment system includes several components which may be used to recruit participants to a clinical trial. The recruitment system may be implemented as a web-based application such as a website which provides information on numerous clinical trials. The website will contain detailed, searchable information on the clinical trials and essentially advertise the clinical trial to a potential participant by providing details on the trial, including who should participate, the location of the trial, the length of the trial, the type of drug, treatment or device being tested, etc. However, the website will be a graphic-based style with visual appeal to the user as opposed to just a laundry list of information. The website may also host a video or other presentation that clearly explains the important information on the clinical trial that a potential participant would be interested in. A user visiting the website can search for a clinical trial based on a particular medical condition, a location of the user and the location of the clinical trial (proximity searching) and many other details relating to the trial, the patient and the treatment.

The website may be designed to guide users to appropriate trials through a series of menus provided on a graphical user interface (GUI) of the website. In one embodiment, the categories of participants listed on a homepage of the website may include patients, healthy volunteers, caregivers, pediatrics, physicians and clinical sponsors. A new user may then be asked to enter their personal profile information, such as their age, weight, height, medical conditions, eating and drinking habits, history or use of smoking, etc. The user may also be able to upload electronic medical records or give the website permission to request access to their EMRs from their doctor or some other type of accessible but secure database. Detailed patient profile information, such as information on the patient's previous experiences in clinical trials, may also be obtained, as this type of profile information may also be useful to identify candidates for related trials on similar or alternative treatments.

The website may also present a bulletin board of available clinical trials that are currently looking for participants. The clinical trials may be listed by category, or may just provide a thumbnail for each category so that a user interested in that category will select the thumbnail to see specific trials. When a certain category is selected, another page will be provided with trials divided by additional more specific types, such as specific conditions, diseases or symptoms that someone is experiencing. For example, selecting a category of "pediatrics" on the homepage will lead to another page where further categories such as "ADHD/ADD, Asthma and Allergy, Bed Wetting, Down Syndrome," etc. are listed. The website may also provide categories for numerous types of conditions regardless of whether a clinical trial is available, and provide a user with the opportunity to sign up for an alert for a future clinical trial. The data on how many users sign up for alerts for particular conditions or treatments may be used by a researcher or medical company to decide which new area of treatment to pursue.

One benefit of the clinical trial recruitment system is the plurality of patient data which is collected, as this data can be used to not only find patients for existing clinical trials, but also to design clinical trials based on identified symptoms and conditions that are prevalent in the patient medical data. Similarly, the value of a potential clinical trial can be evaluated by determining how many potential patients there are in the clinical trial recruitment system database.

In another embodiment, a link on the clinical trial page may also provide a user with the ability to chat or email with an expert who is helping administer the clinical trial and can answer further questions.

At this point, a specific clinical trial may be selected and a new page with details of the clinical trial will be provided, including short videos explaining the trial, a list of eligibility criteria, links to other websites with additional information, and options for enrolling in the clinical trial, following the clinical trial, or sharing the clinical trial with someone else. The website for the clinical trial may also include a message board for potential participants to ask questions or for the current participants to discuss certain aspects of the trial. A communication tool may also be provided for direct communication with a doctor or clinician. A profile of the doctor or doctors running the clinical trial may also be provided so that a patient candidate can evaluate the doctor's history and expertise in a particular field.

In one embodiment, the website may be configured as a social media tool where users and visitors can share information with each other on clinical trials. Users may be provided with rewards for referring a clinical trial to another user that ends up enrolling in the clinical trial or for participating in the clinical trial themselves. In another embodiment, a rewards system may reward a user for posting a hyperlink with information about the clinical trial on their social media page, broadcast feed, etc. if someone clicks on the hyperlink and enrolls in the clinical trial. Similarly, an advertisement for a clinical trial may be populated on a social media website next to a discussion about a particular condition or disease by using a media scrubber to extract user content from the social media website.

In one embodiment, an "e-flyer" may be used as well, so that each person who views the e-flyer and clicks on the e-flyer to can be tracked in order to provide the appropriate reward to the user who originally posted or shared the e-flyer. Tiered rewards may be available to a variety of users depending on how close they are in the chain of referral to the ultimate end-user that signed up for the clinical trial. Options may be provided for users to send short emails or text messages using the website to potential candidates, further simplifying the process of sharing a clinical trial with another user or guest. The rewards may be any type of monetary or non-monetary reward, such as earning points for an online game, receiving gift cards or discounts, etc.

The clinical trial recruitment system may also use targeted advertising to recruit participants, such as by populating ads when a user types in certain words in a search engine query or when a user uses certain words in an email, on a social media website, etc.

In another embodiment, a doctor, clinic or other health care professional or company may use the clinical trial recruitment system to analyze their lists of patients and patient profiles to identify potential participants in the available clinical trials. The doctor may be provided with a software application resident on their local network that can analyze electronic medical records to sort through the various conditions, symptoms and diagnoses for patients, compare them with the profile information on the clinical trials available and then make recommendations for which patients may be interested in or benefit from certain clinical trials. The system may be designed to work with the provider's electronic health records (EHR) and different formats for medical and genomic data. Alternatively, patient data may be uploaded to a remote server which securely stores patient data but which can also provide an analysis of the patient data against the available clinical trials to recommend certain clinical trials for certain patients that may be a good match. This patient matching service may also be automated to be carried out without the direct supervision or input of the doctor, which saves the doctor time while at the same time providing a greater service to the doctor's patients.

As candidates apply for participation in the clinical trial, they are evaluated and screened to ensure that they are a good match for the clinical trial. Several steps of screening may be carried out to slowly narrow down the potential candidates to a select few which exactly match the type of participant that is needed for a particular clinical trial. For example, a first screening step may include basic tests, like demographic data, a patient's diagnosis, previous medical conditions and any test results. The screening steps may be as specific as looking at a genomic profile to determine if a candidate possesses a specific genome sequence that is relevant to the treatment being performed in the clinical trial. Clinical trials may require a specific sub-set of patients with unique symptoms or conditions in order to determine the effectiveness of a particular treatment or device, and so numerous screening steps may be needed.

In one embodiment, the candidates for a particular clinical trial can be ranked using a proprietary scoring system based on how well a candidate patients profile matches the criteria for the clinical trial. The profile and criteria may include anything from the location of the patient and the location of the clinical trial to particular genetic code in the patients genome.

In another embodiment, the clinical trial recruitment system provides for automated follow ups with a patient to evaluate their progress and make assessments. The system may also follow up with users that watch or never enroll in a particular clinical trial in order to determine why they did not enroll and make improvements to the system.

Once a user is enrolled in the clinical trial recruitment system, additional information may be provided to the user, such as analytics on their medical data, coaching and tips for improving their health, and even cautions and warnings for potential side effects or risks of combining incompatible treatments or drugs. Additionally, the patient may be provided with offers for new drugs, treatments, devices, health insurance, patient groups, etc. based on their medical information and the clinical trials they have participated in. The user may also be asked to participate in evaluating the clinical trial and those involved in the clinical trial, in order to provide rankings of the best companies or doctors in the clinical trial industry.

The clinical trial recruitment system is set up to be a neutral host for any type of clinical trial from any company, and the emphasis of the recruitment system will be on helping a patient find the best clinical trial option.

Figure 13:
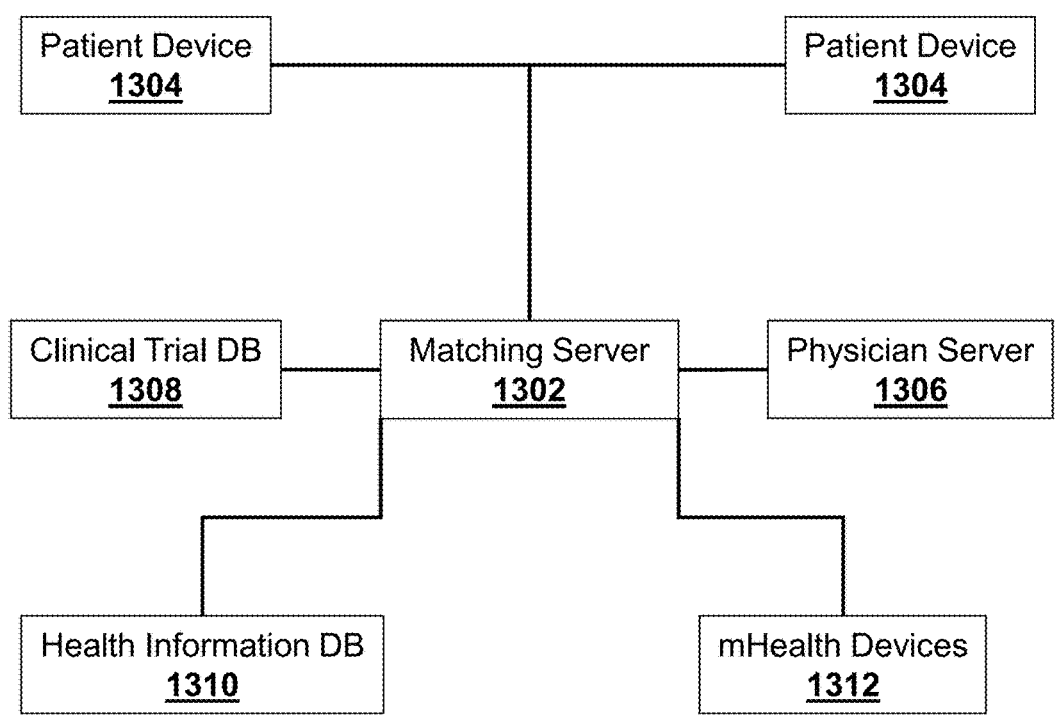
FIG. 13 illustrates a system for recruiting patients for a clinical trial, according to one embodiment.
Figure 14:
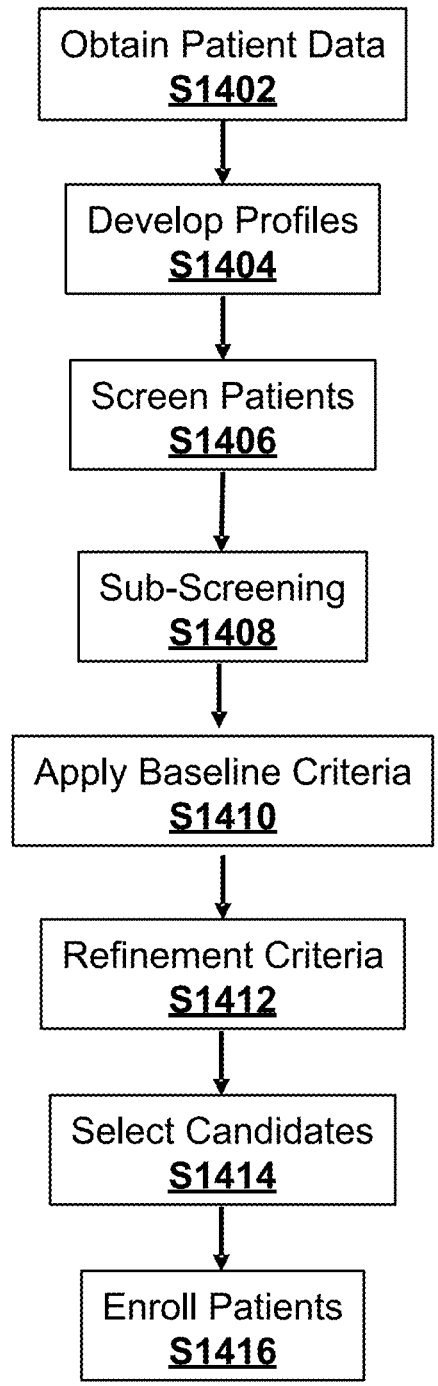
FIG. 14 illustrates a method of screening patients for a clinical trial, according to one embodiment.
Figure 15:
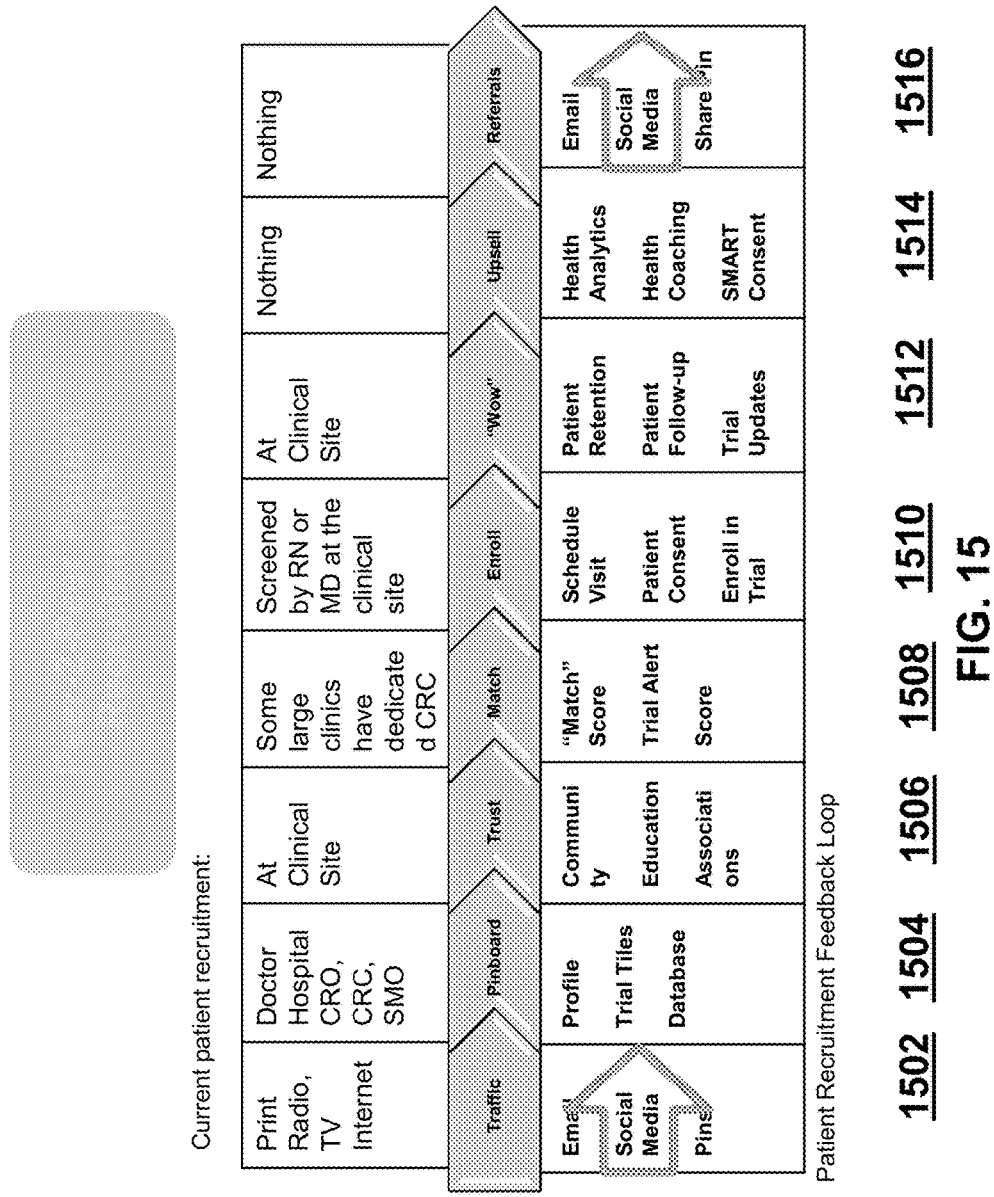
FIG. 15 illustrates a method of recruiting and matching patients for clinical trials, according to one embodiment.

FIGS. 13-15 and the corresponding description of co-pending U.S. patent application Ser. No. 14/214,653, entitled "Systems and methods for recruiting and matching patients for clinical trials, which is incorporated herein by reference as if set forth.

Incorporated are systems and methods provide for recruiting and matching patients for clinical trials using a network-based software platform which publicizes clinical trials, recruits patients for participation in the clinical trials, and obtains patient profile information to match patients with appropriate clinical trials based on compatibility and compliance measurements. Patients may be recruited to join clinical trials through online networking and referrals using social media and other electronic communication managed by the software platform. The software platform provides a user interface where patients can input profile information, search for clinical trials and view interactive clinical trial information pages. Patient profile information and clinical trial information may be analyzed to generate a compatibility score which indicates a patient's compatibility with a particular clinical trial. Additional patient information may be used to generate a compliance score which indicates a patient's likelihood of completing the clinical trial.

In one embodiment, a method for recruiting and matching patients for clinical trials comprises method for recruiting and matching patients with clinical trials, comprising: recruiting one or more patients for participation in a clinical trial; evaluating the compatibility of the one or more patients with the clinical trial and generating a compatibility score; evaluating the compliance of the one or more patients with the clinical trial and generating a compliance score; and determining whether the one or more patients should be enrolled in the clinical trial based on the compatibility score and compliance score.

Embodiments described herein provide systems and methods for recruiting and matching of patients for clinical trials. Patients are recruited through various methods to visit a clinical trial information website with a variety of graphical user interfaces (GUIs) that display information on available clinical trials and provide for patient interaction with the website and various clinical trial information pages. Through the patient interaction with the website, a patient profile is created, which, along with other patient information, can then be used to match patients with appropriate clinical trials and generate a match score reflecting the compatibility of the patient with a particular clinical trial. Additional patient information may be used to determine a compliance score, which refers to the likelihood that the patient will complete the clinical trial.

The use of social media networking for patient recruitment is nascent with limitless potential. Readily available health data on each patient may be stored, and the stored health data for eligible trial participants may be automatically matched with clinical trials that match their health state and or location. Doctors may also be alerted when one of their patients is a match for a trial. The systems and methods described herein use digital health data, social media and analytics to optimize patient recruitment and access to clinical trials. Voluntarily received patient demographic, health and life style information may be leveraged and combined with data from electronic health records and other sources to increase the speed, number and quality of patients recruited for clinical research.

The clinical trial recruitment system is set up to be a neutral host for any type of clinical trial from any company, and the emphasis of the recruitment system will be on helping a patient find the best clinical trial option.

Patient Recruitment System and Method

In one embodiment, a system 1300 for recruiting and matching patients is illustrated in FIG. 13. A patient recruitment platform may be hosted and generated at a matching server 1302, and be connected with one or more patient devices 1304 which are used by patients to access the clinical trial information website at the matching server 1302. In addition to being connected with the matching server 1302, the patient devices 1304 may also be connected with each other, enabling communication between patients with regard to potentially-matching clinical trials. The matching server 1302 may also be connected over a network with a physician server 1306 run by a physician, a clinical trial database 1308, a health information database 1310 or any type of mHealth device 1312. Each of the servers, databases or devices may be a source of personal health information such as would be found in a clinic, hospital, etc. which has a plurality of patient information stored therein in the form of electronic medical records (EMRs) and Personal Health Records (PHR). Examples of the health information database 1310 include a physician investigator (PI) database, a protocol database or Electronic Health Record (EHR) database. The patient information from the physician server 1306 may be shared with the matching server 1302 and used to improve matches between the patients and the clinical trials. Each of the matching server 1302, patient devices 1304 and physician server 1306 may be embodied on a computer with a processor and memory Patients will use the patient recruitment platform to identify and apply for clinical trials. As candidates apply for participation in the clinical trial, they are evaluated and screened to ensure that they are a good match for the clinical trial. Several steps of screening may be carried out to slowly narrow down the potential candidates to a select few which exactly match the type of participant that is needed for a particular clinical trial.

FIG. 14 illustrates one embodiment of a method of screening patients for a clinical trial. First, patient data is obtained in S1402, after which a patient profile is developed in S1404 which is then used to perform an initial screening step S1406. For example, a first screening step may include basic tests, like demographic data, a patient's diagnosis, previous medical conditions and any test results. The screening steps may be as specific as looking at a genomic profile to determine if a candidate possesses a specific genome sequence that is relevant to the treatment being performed in the clinical trial. Clinical trials may require a specific sub-set of patients with unique symptoms or conditions in order to determine the effectiveness of a particular treatment or device, and so numerous screening steps may be needed. An initial screening step to screen all patients is followed by a sub-selection step S1408 which has narrowed down the entire group of candidates to only 20. A set of baseline criteria pertaining to the specific physiological or symptomatic conditions needed for the clinical trial is then applied in step S1410, which further narrows the candidate patients to only 5. In a further refinement step S1412, even more specific criteria may be applied to identify specific levels of compounds in a patient's body. These further refinement steps may require information not included in a patient's profile information and therefore require the patient to come to a physician's office for specific testing of the patient. After this further refinement step, only the few patients that remain are selected in step S1414 and enrolled (S1416) in the clinical trial.

FIG. 15 illustrates one embodiment of the overall method of recruiting and matching a patient with a clinical trial. Beginning with the left side of the diagram, overall recruitment of patients begins with marketing and publication techniques, such as advertisements in print, radio, television and the Internet (302). These marketing efforts may also include the tools provided to patients within the patient recruitment system 1504, including sending messages from one patient to another, posting information about a clinical trial to a board or message board of specific patients, and publication over social media. E-mail blasts may be sent out to an overall list of patients who are interested in clinical trials, or to doctors, hospitals and clinics that have patients who may be interested in enrolling in a clinical trial.

Any leads captured during this initial process are then taken for further processing within the system to build trust 1506, such as having the candidate patient review the information on the clinical trial available at the clinical trial website. The candidate patient is also able to communicate with a person knowledgeable about the clinical trial to have any questions answered. This additional level of information provided to the candidate will build trust between the candidate and the clinical trial and help to attract more candidate patients.

Next, at 1508 the patients who are interested in enrollment are evaluated based on patient profile information to determine both a "match score" and a "compliance score" (shown here as a "score"). These scores, as described in further detail below, provide a simple numerical value reflecting the likelihood that a particular patient will be a successful participant in the clinical trial. If the patient is a match, an alert may be sent to the patient indicating their approval and asking that they enroll.

Approved patients may then enroll 1510 by scheduling a visit at the clinical trial location or with a physician who will carry out a further examination of the patient to make sure they are appropriate candidates for the clinical trial. The patients who are finally enrolled and begin participating in the clinical trial are still provided with services 1512 from the patient recruitment system, in terms of communication with the clinical trial sponsors or physicians, messages with updates and scheduling for trial participation, evaluations of the clinical trial, reviews and other feedback.

At the end of the clinical trial period, the patient may still be provided with additional services 1514 to ensure that they remain interested in the patient recruitment system. These services may include overall health analytics, coaching, and rewards and incentives for evaluating the trial and the physician. The patient is then motivated and incentivized to share their experience in the clinical trial 1516 with others via the website, social media, messaging and other communication methods. By generating positive patient experiences, patients will increase the publicity of the website and the potential patient base from which the clinical trials select their patients.

Interactive Clinical Trial Platform

In one embodiment, an interactive clinical trial platform may be provided in the form of a web-based application such as a website hosted at the matching server and accessible by patients on their patient devices. The website may provide information on numerous clinical trials which the clinical trial sponsor has specifically uploaded to the website or which are aggregated from other content on the Internet, such as a clinical sponsor's primary website.

Further embodiments of a clinical trial information page that the website may provide for each listed clinical trial. The website will contain detailed, searchable information on the clinical trials and essentially advertise the clinical trial to a potential patient by providing details on the trial, including who should participate, the location of the trial, the length of the trial, the type of drug, treatment or device being tested, etc. However, the website will be a graphic-based style with visual appeal to the user as opposed to just a laundry list of information. The website may also host a video or other presentation that clearly explains the important information on the clinical trial that a potential participant would be interested in.

The website may also have search capabilities so that a patient visiting the website can search for a clinical trial based on a particular medical condition, based on a location of the user and the location of the clinical trial (proximity searching) and many other details relating to the trial, the patient and the treatment. In another embodiment, the website may present the patient with a screening application which helps the patient identify their symptoms, possible causes and other relevant health and medical information that will provide a more suitable clinical trial.

The website may be designed to guide users to appropriate trials through a series of menus provided on a graphical user interface (GUI) of the website. In one embodiment, the categories of participants listed on a homepage of the website may include patients, healthy volunteers, caregivers, pediatrics, physicians and clinical sponsors. Each type of participant will select their corresponding icon in order to view a more specific page of information directed specifically to their group.

The website may also present a bulletin board of available clinical trials that are currently looking for participants. The clinical trials may be listed by category, or may just provide a hyperlinked thumbnail image or icon for each category so that a user interested in that category will select the thumbnail image to open a new page with more specifics on the particular type of clinical trials.

When a certain category is selected, another page will be provided with trials divided by additional more specific types, such as specific conditions, diseases or symptoms that someone is experiencing. For example, selecting a category of "pediatrics" on the homepage, as described above, leads to another page where further categories such as "ADHD/ADD, Asthma and Allergy, Bed Wetting, Down Syndrome," etc. are listed.

In one embodiment, the website may also provide categories for numerous types of conditions regardless of whether a clinical trial is available, in which case the user is provided with the opportunity to sign up for an alert for a future clinical trial. In another embodiment, the patient can sign up to receive alerts and updates on the enrollment process for the clinical trial so the user can have time to decide whether or not to participate in the trial. The data on how many users sign up for alerts for particular conditions or treatments may be used by a researcher or medical company to decide which new area of treatment to pursue.

In another embodiment, a link on the clinical trial page may also provide a user with the ability to chat or email with an expert who is helping administer the clinical trial and can answer further questions.

Once the patient has viewed the clinical trial information page and its content, the user may select to either "enroll" in the clinical trial, "follow" the clinical trial (for future announcements and news), or share the information on the clinical trial with another patient that may be interested, such as a friend or family member that suffers from the same disease.

At this point, a specific clinical trial may be selected and a new page with details of the clinical trial will be provided, including short videos explaining the trial, a list of eligibility criteria, links to other websites with additional information, and options for enrolling in the clinical trial, following the clinical trial, or sharing the clinical trial with someone else. The website for the clinical trial may also include a message board for potential participants to ask questions or for the current participants to discuss certain aspects of the trial. A communication tool may also be provided for direct communication with a doctor or clinician. A profile of the doctor or doctors running the clinical trial may also be provided so that a patient candidate can evaluate the doctor's history and expertise in a particular field.

Recruitment and Sharing

The recruiting of patients by other patients and doctors is of paramount importance for the success of the patient recruitment system. Both patients and doctors may be involved in the recruitment of patients, as well as overall medical practices, hospitals and other healthcare facilities. Social networking, messaging through text, e-mail, instant messaging other messaging protocols may all be used by patients in order to share a particular clinical trial and generate a referral.

In one embodiment, the website may be configured as a social media tool where users and visitors can share information with each other on clinical trials. One embodiment where a message can be created by one patient and sent to another patient suggesting that a particular clinical trial may be beneficial to the receiving patient.

In another embodiment, patients may be rewarded for certain activities related to recruiting other patients or providing feedback relating to their experience with a clinical trial. Users may be provided with rewards for referring a clinical trial to another user that ends up enrolling in the clinical trial or for participating in the clinical trial themselves. In another embodiment, a rewards system may reward a user for posting a hyperlink with information about the clinical trial on their social media page, broadcast feed, etc. if someone clicks on the hyperlink and enrolls in the clinical trial. Similarly, an advertisement for a clinical trial may be populated on a social media website next to a discussion about a particular condition or disease by using a media scrubber to extract user content from the social media website.

In one embodiment, a traceable "e-flyer" may be used as well, so that each person who views the e-flyer and clicks on the e-flyer to can be tracked in order to provide the appropriate reward to the user who originally posted or shared the e-flyer. Tiered rewards may be available to a variety of users depending on how close they are in the chain of referral to the ultimate end-user that signed up for the clinical trial. Options may be provided for users to send short emails or text messages using the website to potential candidates, further simplifying the process of sharing a clinical trial with another user or guest. The rewards may be any type of monetary or non-monetary reward, such as earning points for an online game, receiving gift cards or discounts, making donations to charity, etc.

The clinical trial recruitment system may also use targeted advertising to recruit participants, such as by populating ads when a user types in certain words in a search engine query or when a user uses certain words in an email, on a social media website, etc.

Enrollment and Profiling

Once the patient has decided to enroll in a particular clinical trial, the system provides a streamlined and simplistic process where the patient completes a set of information on their health and wellness. The patient profile process may be performed by a screening application running at the patient device or the matching server which takes the patient step-by-step through a process of selecting different information about the patient's health, wellness and specific problems being experienced. During the enrollment process, a patient profile is generated which may include patient health data provided by the patient during an enrollment. The patient profile can also be populated with third-party medical information on the patient, such as Electronic Medical Records (EMRs) kept by the patient's primary care doctor at the physician server or personal health records (PHRs) or mHealth devices that monitor and record patient data (such as Zeo, Garmin or MS Health Vault).

In one embodiment, patient medical data from the patient's medical records or information provided by the patient may be used for the clinical trial recruitment system. The patient's medical data may be stored in a database at the physician server, which can be easily accessed by the matching server which can be searched by a company running a clinical trial to identify potential candidates for participation in the clinical trial.

To create the patient profile, a new user may then be asked to enter their personal profile information, such as their age, weight, height, medical conditions, eating and drinking habits, history or use of smoking, etc. Information on the patient's location may also be needed in order to customize the selection of available clinical trials to those within a certain city, county or region near the patient. The user may also be able to upload electronic medical records or give the website permission to request access to their EMRs from their doctor or some other type of accessible but secure database.

Detailed patient profile information, such as information on the patient's previous experiences in clinical trials, may also be obtained, as this type of profile information may also be useful to identify candidates for related trials on similar or alternative treatments.

The patient enrollment application may also provide an interactive scheduling tool which allows the patient to immediately see upcoming available times in which the patient may need to meet with the clinical trial sponsor or physician investigator (PI) to discuss the treatment.

Once the patient profiles are created, the amount of data collected during the patient enrollment process may be stored in a local database of the matching server. This large sum of data could be exploited in numerous different ways beyond the scope of patient recruitment, as the amount of collective health information available for such a large number of patients may prove useful to study for medical purposes, some of which will be described further herein.

Match Score

In one embodiment, the candidates for a particular clinical trial can be ranked with a match score using a proprietary scoring system based on how well a candidate patient's profile matches the criteria for the clinical trial. The profile and criteria may include anything from the location of the patient and the location of the clinical trial to particular genetic code in the patient's genome. The screening process will quickly and easily screen patients for clinical trials based on inclusion and exclusion rules provided by a clinical trial sponsor, which will then be cross-referenced with the patient profile data, linked EMR/EHR data and other questions specific to a particular clinical trial. The match score represents a simple numerical value of all of these evaluations.

A match score represents a candidate patient's compatibility with a particular clinical trial based on a comparison of the candidate patient's profile information with the criteria and goals of the clinical trial. The clinical trial will list several criteria which set forth the type of patients needed for the trial, such as age, gender, symptoms, medications, etc. The criteria list is then compared with the patient profile information to determine how many of these criteria match the patient's profile information.

For example, if a study protocol needed patients with a minimum of 5 out of 10 criteria, such as being on a type of drug, having a body mass index above a specific number, etc., the match score is a direct correlation to the needed criteria. The match score may therefore be given as a ratio, such as 5 out of 10. Additional matches may be reviewed based on the location of the patient to the location of the clinical trial to ensure that the patient is close enough to the clinical trial to participate.

In another embodiment, a doctor, clinic or other health care professional or company may use the clinical trial recruitment system to analyze their lists of patients and patient profiles to identify potential participants in the available clinical trials. The doctor may be provided with a software application resident on their local network that can analyze electronic medical records to sort through the various conditions, symptoms and diagnoses for patients, compare them with the profile information on the clinical trials available and then make recommendations for which patients may be interested in or benefit from certain clinical trials. The system may be designed to work with the provider's electronic health records (EHR) and different formats for medical and genomic data. Alternatively, patient data may be uploaded to a remote server which securely stores patient data but which can also provide an analysis of the patient data against the available clinical trials to recommend certain clinical trials for certain patients that may be a good match. This patient matching service may also be automated to be carried out without the direct supervision or input of the doctor, which saves the doctor time while at the same time providing a greater service to the doctor's patients.

Compliance Score

A compliance score can assess a candidate patient's likelihood of complying with the requirements of the clinical trial and completing the clinical trial with an adequate amount of feedback. For example, if a patient has enrolled in 5 trials in the past but only completed 3 trials, the patient will be given a rating of 3 out of 5. The patients and the physicians will be provided with a score that is continually updated by proprietary algorithms to predict the likelihood of a patient: 1) entering a trial (enrollment), 2) being compliant (good data), 3) completing a trial (achieving a data point for the study), and 4) sharing trial information with a network (outreach ability of the user or physician).

The information used to determine the compliance score may be obtained from data on the patient reported by previous clinical trials, patient surveys, public data including correlated social media postings attributed to the patient and other user generated data.

In one embodiment, the physicians, sponsors or research group conducting the clinical trial can also be rated and provided with a compliance score by the patients participating in the clinical trial. This information can then be displayed on the clinical trial page for any future clinical trial conducted by that physician, sponsor or research group so that patients can see if the clinical trial has a good service or track record of conducting clinical trials. In addition, this information will be useful to sponsors looking for physicians and clinical (or contract) research organizations (CROs) to conduct new clinical trials.

In another embodiment, the clinical trial recruitment system provides for automated follow ups with a patient to evaluate their progress and make assessments. The system may also follow up with users that watch or never enroll in a particular clinical trial in order to determine why they did not enroll and make improvements to the system. The system may also specifically follow up with patients who dropped out of trials after they started, as this information may be critical when the trial sponsor is providing the clinical trial results to a government or regulatory agency.

Patient and Trial Matching Process

One embodiment of a method for matching patients with clinical trials, where patient data is obtained and used to develop patient profiles. Clinical trial data is also obtained and used to develop clinical trial profiles. The profiles are then compared to identify similar categories and produce likely matches based on the similarities in one or more categories of the profiles. Either the patient or the clinical trial is then notified about the potential match, depending on which party initiated the request or which party is interested in finding a match.

An alternate method of patient and clinical trial matching can include where the patient is directed to interact with a user interface in real time to answer general questions about health, disease, location, availability, etc., which is then used in real time to compare with stored information on clinical trials and prompt the user to answer detailed health questions based on their answers to the previous questions and based on any preliminary matching clinical trials. These detailed answers will then be used to determine one or more matching clinical trials which match the information input by the user. In this alternate method, the user does not need to upload any personal health information or personally identify themselves, thus providing an easier method to obtain a match without requiring the use of EHR or other medical records which may be difficult to obtain or require regulatory hurdles to use.

Additionally, a graphical user interfaces (GUIs) of a clinical trial matching process can be included according to embodiments. For example, a user is provided with different tiles for different types of diseases, symptoms, injuries, etc, and asked to create a profile in order to begin the process. The profile screen may collect anonymous health information or location information to select a local trial. An initial match screen is is generated based on the use profile created in the previous step. The user can select one of the trials and see detailed information about the trial, including the likely candidates, the length, location, compensation, etc. If the user is interested, the user can select to be "pre-screened" for the trial in order to see if they fit a specific trial criteria. Additionally, options to chat with an advisor are provided or share the trial information with a likely candidate. In one embodiment, the user's social media information and contacts' information may be utilized to suggest social media contacts in certain locations that may be interested in a clinical trial listed in the results.

If the user decides to be pre-screened, detailed information is then collected to determine whether the user meets the specific criteria for the trial. If the user is a match, a match screen is produced, inviting the user to chat with a representative to discuss enrollment, or proceed to enrollment and schedule an appointment with a physician investigator (PI). If the trial is not a match, the non-match screen is produced, inviting the user to re-run the match process. The user is shown the location of the trials to pick the best option for an appointment, and the user is given an interactive user interface to schedule an appointment.

In an embodiment a trial match tab which provides a detailed list of information on various trials, the status/phase of the trial, the number of matches that have been provided by the system for that particular trial, enrollment deadlines and sponsor/CRO information. In another example, a Site Match tab with detailed information on clinical trial sites, including the number of matches, total patients, number of PIs, location/zip code and the rating or score for that particular site, based on previous user ratings of the site.

Clinical Trial Design & Feasibility Analytics

One benefit of the clinical trial recruitment system is the plurality of patient data which is collected, as this data can be used to not only find patients for existing clinical trials, but also to design clinical trials based on identified symptoms and conditions that are prevalent in the patient medical data. Similarly, the value of a potential clinical trial can be evaluated by determining how many potential patients there are in the clinical trial recruitment system database. A "test-run" of a clinical trial could even be conducted by searching the database of patient profile information to determine how many candidates exist for a given set of criteria of a proposed clinical trial. Sponsors of the clinical trial may then shift the location of the clinical trial or adjust their criteria to find a predicted set of patients that meets their minimum requirements.

A feasibility determination may also be made to determine whether a clinical trial is likely to find enough patients in a particular area or with a particular CRO based on patient and enrollment data that is stored in the system from previous clinical trials.

Clinical Trial Analytics

In one embodiment, data can be obtained on the clinical trial based on past analytics of similar trials run by similar companies or physician investigators. The clinical trial sponsors and managers may be given ratings based on previous performance, which can then be utilized by the patients selecting the trials to determine which trial may be better managed and more likely to produce a potentially successful result.

Dashboards may be provided for a patient or physician investigator to illustrate the relevant information on the trials, matches, contacts and other information relevant to their participation in the matching system. The patients and physicians may be rated and ranked based on relevant reviews of their performance in the clinical trials. An overall CRO/Pharma Dashboard that gives an overview of one or more clinical trials being sponsored by the CRO, including statistics on the types of interest being generated by the match system, the PI, doctor and patient statistics of their candidates and matches, etc., in order to help evaluate the usefulness of their clinical trial and the matching being provided.

Patient Services

Once a user is enrolled in the clinical trial recruitment system, additional information may be provided to the user, such as analytics on their medical data, coaching and tips for improving their health, and even cautions and warnings for potential side effects or risks of combining incompatible treatments or drugs. Additionally, the patient may be provided with offers for new drugs, treatments, devices, health insurance, patient groups, etc. based on their medical information and the clinical trials they have participated in. The user may also be asked to participate in evaluating the clinical trial and those involved in the clinical trial, in order to provide rankings of the best companies or doctors in the clinical trial industry.

Clinical Trial Physician Training

In one embodiment, the patient recruitment system may be adapted to provide training for physicians that host clinical trials. The information obtained from patient evaluations and other patient data relating to clinical trials may be used as a basis for a course which provides education to physicians for conducting successful clinical trials. If a physician completes the course, they may be given a special designation on the website that candidate patients will see when evaluating a particular clinical trial.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed is:

1. A system for managing one or more clinical protocols across multiple locations, comprising:
    a processor;
    a data store configured to store workflow items with information for clinical trials employing the one or more clinical protocols; and
    a memory communicatively coupled with the processor, the memory configured to store instructions, the instructions configured to cause the processor to:
        determine a geo-fence around a first geographic location, wherein the first geographic location is a clinical research location;
        receive, from a mobile device, a second geographic location of the mobile device;
        determine that the mobile device is associated with a clinical trial based at least in part on the first geographic location and the second geographic location;
        determine a plurality of clinical protocol activities associated with the clinical trial and the mobile device;
        determine that the second geographic location of the mobile device satisfies a first clinical protocol activity of the plurality of clinical protocol activities associated with the clinical trial;
        capture a second type of content from the mobile device, wherein the second type of content is associated with a second clinical protocol activity of the plurality of clinical protocol activities;
        determine an additional workflow step for the second clinical protocol activity of the plurality of clinical protocol activities; and
        enable a mobile control interface to display the additional workflow step for the second clinical protocol activity of the plurality of clinical protocol activities, wherein the mobile control interface is located at the first geographic location of the clinical research location.

2. The system of claim 1, wherein the mobile control interface comprises contextual messaging of devices associated with each of the clinical protocols, wherein devices associated with each of the clinical protocols comprise at least one of participant devices, practitioner devices, or facility based systems.

3. The system of claim 2, wherein the contextual messaging is based on the participant devices or the practitioner devices detected within a radius of the clinical research location.

4. The system of claim 1, wherein the additional workflow step comprising at least one of acknowledgement, modification, signature, or assignment.

5. The system of claim 1, wherein information for the additional workflow step is sent via a contextual message, using the mobile control interface, to one or more devices associated with the clinical protocols.

6. The system of claim 1, wherein the mobile control interface further comprises tracking of protocol activities for participants associated with the clinical research location for each clinical protocol.

7. The system of claim 1, wherein the mobile control interface further comprises analytics for each clinical protocol across multiple clinical research locations.

8. A method, comprising:
    determining a geo-fence around a first geographic location, wherein the first geographic location is a clinical research location;
    receiving, from a mobile device, a second geographic location of the mobile device;
    determining that the mobile device is associated with a clinical trial;
    determining a plurality of clinical protocol activities associated with the clinical trial and the mobile device;
    determining that the second geographic location of the mobile device satisfies a first clinical protocol activity of the plurality of clinical protocol activities associated with the clinical trial;
    capturing a second type of content from the mobile device, wherein the second type of content is associated with a second clinical protocol activity of the plurality of clinical protocol activities;
    determine an additional workflow step for the second clinical protocol activity of the plurality of clinical protocol activities; and
    enabling a mobile control interface to display the additional workflow step for the second clinical protocol activity of the plurality of clinical protocol activities, wherein the mobile control interface is located at the first geographic location of the clinical research location.

9. The method of claim 8, wherein the mobile control interface comprises contextual messaging of devices associated with each of the clinical protocols, wherein devices associated with each of the clinical protocols comprise at least one of participant devices, practitioner devices, or facility based systems.

10. The method of claim 9, wherein the contextual messaging is based on the participant devices or the practitioner devices detected within a radius of the clinical research location.

11. The method of claim 8, wherein the additional workflow step comprising at least one of acknowledgement, modification, signature, or assignment.

12. The method of claim 8, wherein information for the additional workflow step is sent via a contextual message, using the mobile control interface, to one or more devices associated with the clinical protocols.

13. The method of claim 8, wherein the mobile control interface further comprises tracking of protocol activities for participants associated with the clinical research location for each clinical protocol.

14. The method of claim 8, wherein the mobile control interface further comprises analytics for each clinical protocol across multiple clinical research locations.

15. The system of claim 1, wherein the additional workflow step is determined based at least in part on the second geographic location of the mobile device.

16. The system of claim 1, wherein the second type of content from the mobile device comprises a time duration that the mobile device is visiting the clinical research location.

17. The system of claim 1, further comprising:
enable a platform module to display information associated with the clinical research location at the mobile device.

* * * * *